(12) United States Patent
Yudin et al.

(10) Patent No.: US 10,703,779 B2
(45) Date of Patent: Jul. 7, 2020

(54) OXADIAZOLE CYCLIC PEPTIDES

(71) Applicant: THE GOVERNING COUNCIL OF THE UNIVERSITY OF TORONTO, Toronto (CA)

(72) Inventors: Andrei Yudin, Oakville (CA); John R. Frost, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 15/760,533

(22) PCT Filed: Sep. 16, 2016

(86) PCT No.: PCT/CA2016/000234
§ 371 (c)(1),
(2) Date: Mar. 15, 2018

(87) PCT Pub. No.: WO2017/045063
PCT Pub. Date: Mar. 23, 2017

(65) Prior Publication Data
US 2018/0251496 A1  Sep. 6, 2018

Related U.S. Application Data

(60) Provisional application No. 62/220,934, filed on Sep. 18, 2015.

(51) Int. Cl.
*C07K 7/64* (2006.01)
*C07K 1/02* (2006.01)
*C07D 498/18* (2006.01)
*C07K 7/06* (2006.01)

(52) U.S. Cl.
CPC .............. *C07K 7/64* (2013.01); *C07D 498/18* (2013.01); *C07K 1/02* (2013.01); *C07K 7/06* (2013.01)

(58) Field of Classification Search
CPC ........... C07K 7/64; C07K 7/06; C07D 498/18
See application file for complete search history.

(56) References Cited

PUBLICATIONS

Frost. Nature Chemistry, 2016, 8, 1105-1111, published Oct. 24, 2016 (Year: 2016).*
Adib, et al., "One-Pot Four-Component Synthesis of N²-Alkyl-N³-[-(1,3,4-oxadiazol-2-yl)aryl]benzofuran-2,3-diamines," *Helvetica Chimica Acta*, 95: 788-794, 2012.
Ali, et al., "Conformationally Constrained Peptides and Semipeptides Derived from RGD as Potent Inhibitors of the Platelet Fibrinogen Receptor and Platelet Aggregation," *Journal of Medicinal Chemistry*, 37: 769-780, 1994.
Assem, et al., "Role of Reversible Dimerization in Reactions of Amphoteric Aziridine Aldehydes," *Journal of Organic Chemistry*, 77: 5613-5623, 2012.
Bio, et al., "An Improved Synthesis of N-Isocyanoiminotriphenylphosphorane and Its Use in the Preparation of Diazoketones," *Synthesis*, 1: 19-21: 2005.
Biron, et al., "Improving Oral Bioavailability of Peptides by Multiple N-Methylation: Somatostatin Analogues," *Angewandte Chemie*, 47: 2595-2599, 2008.
Borg, et al., "Synthesis of 1,2,4-Oxadiazole-, 1,3,4-Oxadiazole-, and 1,2,4-Triazole-Derived Dipeptidomimetics," *Journal of Organic Chemistry*, 60: 3112-3120, 1995.
Cody, et al., "Design of a Potent Combined Pseudopeptide Endothelin-A/Endothelin-B Receptor Antagonist, Ac-DBhg[16-Leu-Asp-Ile-[NMe]Ile-Trp21] (PD 156252): Examination of Its Pharmacokinetic and Spectral Properties," *Journal of Medicinal Chemistry*, 40: 2228-2240, 1997.
Cossio, et al., "Mechanism and Stereoselectivity of the Aza-Wittig Reaction Between Phosphazenes and Aldehydes," *Journal of Organic Chemistry*, 71: 2839-2847, 2006.
Doedens, et al., "Multiple N-Methylation of MT-II Backbone Amide Bonds Leads to Melanocortin Receptor Subtype hMC1R Selectivity; Pharmacological and Conformational Studies," *Journal of the American Chemical Society*, 132,: 8115-8128, 2010.
Driggers, et al., "The Exploration of Macrocycles for Drug Recovery—An Underexploited Structural Class," *Nature*, 7: 608-624, 2008.
Frank, et al., "Natural Macrocyclic Molecules Have a Possible Limited Structural Diversity," *Mol Divers*, 11:115-118, 2007.
Haviv, et al., "Effect of N-Methyl Substitution of the Peptide Bonds in Luteinizing Hormone-Releasing Hormone Agonists," *Journal of Medicinal Chemistry*, 36: 363-369, 1993.
Haviv, et al., "The Effect of NMeTyr⁵ Substitution in Leteinizing Hormone-Releasing Hormone Antagonists," *Journal of Medicinal Chemistry*, 36: 928-933, 1993.
He & Yudin, et al., "Amphoteric α-Boryl Aldehydes," *Journal of the American Chemical Society*, 133: 13770-13773.
Hewitt, et al., "Cell-Permeable Cyclic Peptides from Synthetic Libraries Inspired by Natural Products," *Journal of the American Chemical Society*, 137: 715-721, 2015.
Hili & Yudin, "Readily Available Unprotected Amino Aldehydes," *Journal of the American Chemical Society*, 128,: 14772-14773, 2006.
Hili, et al., "Macrocyclization of Linear Peptides Enabled by Amphoteric Molecules," *Journal of the American Chemical Society*, 132: 2889-2891, 2010.
International Search Report and Written Opinion Issued in Corresponding PCT Application No. PCT/CA2016/000264, dated Dec. 9, 2016.
Katsara, et al., "Round and Round We Go: Cyclic Peptides in Disease," *Current Medicinal Chemistry*, 13: 2221-2232, 2006.
Marsault & Peterson, "Macrocycles Are Great Cycles: Applications, Opportunities, and Challenges of Synthetic Macrocycles in Drug Discovery," *Journal of Medicinal Chemistry*, 54: 1961-2004, 2011.

(Continued)

*Primary Examiner* — Noble E Jarrell
(74) *Attorney, Agent, or Firm* — Norton Rose Fulbright US LLP

(57) ABSTRACT

The present invention relates to cyclic amino acid molecules, in particular 1,3,4-oxadiazole containing macrocyclic peptides, and a process to produce the same. The process involves the macrocyclization of amino acids or linear peptides. Specifically, the process comprises reacting an amino acid molecule with an isocyano-iminophosphorane and an aldehyde or a ketone.

27 Claims, 10 Drawing Sheets
Specification includes a Sequence Listing.

(56) References Cited

PUBLICATIONS

Mas-Moruno, et al., "Cilengitide: The First Anti-Angiogenic Small Molecule Drug Candidate/Design, Synthesis, and Clinical Evaluation," *Anti-Cancer Agents in Medicinal Chemistry*, 10: 753-768, 2010.

Nolan & Walsh, "How Nature Morphs Peptide Scaffolds into Antibiotics," *ChemBioChem*, 10: 34-53, 2009.

Ovadia, et al., "The Effect of Multiple N-Methylation on Intestinal Permeability of Cyclic Hexapeptides," *Molecular Pharmaceutics*, 8: 479-487, 2011.

Ramazani & Rezaei, "Novel One-Pot, Four-Component Condensation Reaction: An Efficient Approach for the Synthesis of 2,5-Disubstituted 1,3,4-Oxadiazole Derivatives by a Ugi-4CR/aza-Wittig Sequence," *Organic Letters*, 12(12): 2852-2855, 2010.

Schreiber & Crabtree, "The Mechanism of Action of Cyclosporin A and FK506," *Immunology Today*, 13(4): 136-142, 1992.

Stolzenberg, et al., "Free and Metal-Coordinated (N-Isocyanimino)trphenylphosphorane: X-ray Structures and Selected Reactions," *European Journal of Inorganic Chemistry*,: 4263-4271, 2005.

Weinberger & Fehlhammer, "N-Isocyanoiminotriphenylphosphorane: Synthesis, Coordination Chemistry, and Reactions at the Metal," *Angewandte Chemie*, 19(6), 480-481,1980.

Wessjohann, et al., "What Can a Chemist Learn from Nature's Macrocycles?—A Brief, Conceptual View," *Molecular Diversity*, 9: 171-186, 2005.

White, et al., "On-Resin N-Methylation of Cyclic Peptides for Discovery of Orally Bioavailable Scaffolds," *Nature Chemical Biology*, 7: 810-817, 2011.

Yudin, "Macrocycles: Lessons from the Distant Past, Recent Developments, and Future Directions," *Chemical Science*, 6: 30-49, 2015.

Zaretsky, et al., "Exocyclic Control of Turn Induction in Macrocyclic Peptide Scaffolds," *Chemistry A European Journal*, 19: 17668-17672, 2013.

Extended European Search Report Issued in Corresponding European Application No. 16845414.8, dated May 9, 2019.

* cited by examiner

| Residue NH | ppb K$^{-1}$ |
|---|---|
| Ser 2 | 1.64 |
| Leu 3 | 5.25 |
| Tyr 4 | 4.12 |
| Gly 5 | 1.12 |

Crystallographic Data for *cyclo*[PGLGF]odz/ethyl (1)

| Entry | R1 | R2 | R3 | R4 | R5 | -logP_e |
|---|---|---|---|---|---|---|
| 1 | -CH$_2$CH$_3$ | -H | -H | | | 5.81 |
| 2 | -CH$_2$CH$_3$ | -H | -CH$_3$ | | | 5.96 |
| 3 | -CH$_2$CH$_3$ | -CH$_3$ | -H | | | 5.42 |
| 4 | -CH$_2$CH$_3$ | -CH$_3$ | -CH$_3$ | | | 5.47 |
| 5 | -CH$_2$CH$_3$ | -CH$_2$Ph | -CH$_2$CH(CH$_3$)$_2$ | | | 4.89 |
| 6 | -CH$_2$Ph | -H | -H | | | 5.27 |
| 7 | -CH$_2$CH(CH$_3$)$_2$ | -H | -H | | | 5.27 |
| 8 | | | | -H | -H | 6.89 |
| 9 | | | | -H | -CH$_3$ | 8.06 |
| 10 | | | | -CH$_3$ | -H | 7.13 |
| 11 | | | | -CH$_3$ | -CH$_3$ | 7.33 |
| 12 | | | | -CH$_2$Ph | -CH$_2$CH(CH$_3$)$_2$ | 4.94 |

OXADIAZOLE CYCLIC PEPTIDES

CROSS-REFERENCE TO RELATED APPLICATIONS

This application is a national phase application under 35 U.S.C. § 371 of International Application No. PCT/CA2016/000234 filed Sep. 16, 2016 which claims priority to U.S. Application No. 62/220,934 filed Sep. 18, 2015; the entire contents of each disclosure is specifically incorporated by reference herein without disclaimer.

FIELD

The present invention relates to cyclic amino acid molecules and methods of preparing the same, and in particular the macrocyclization of amino acids or linear peptides.

BACKGROUND

Cyclic topology is a common motif in natural product structures.[1] A subset of natural products, cyclic peptides, display a wide variety of biological activities, and unique conformational properties due to their circular architecture.[2-6] In 2010, a multicomponent peptide macrocyclization reaction mediated by aziridine aldehydes was reported. These amphoteric species incorporate a nucleophilic amino group and electrophilic aldehyde.[2-8] The final macrolactamization step, which involved a transannular attack by the exocyclic NH aziridine on a mixed anhydride intermediate, furnished a N-acyl aziridine containing macrocycle with an exocyclic amide bond. The non-canonical exocyclic amide moiety was later found to modulate a well defined intramolecular hydrogen bonding network.[9] The success of this multicomponent macrocyclization reaction relies upon on the reversible dimerization of the aziridine-aldehyde monomer, which allowed both aziridine and aldehyde functional groups to maintain independent reactivity.[10]

However, improved macrocyclization processes are desirable.

SUMMARY OF THE INVENTION

In an embodiment, there is disclosed a cyclic molecule of formula [(I)]:

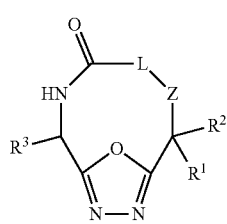

wherein,
Z is an amino terminus of an amino acid;
—C═O— is a carboxy terminus of an amino acid;
L, along with Z and —C═O— is an amino acid molecule;
$R^1$ and $R^2$ are each independently hydrogen or an organic group;
$R^3$ is equivalent to an amino acid side-chain; and
the amino acid molecule is a linear peptide or a salt of the foregoing.

In another embodiment, there is disclosed a process to produce a cyclic amino acid molecule comprising reacting an amino acid molecule, having an amino terminus and a carboxyl terminus, with an isocyano-iminophosphorane having the formula [(II)]:

and a compound having the formula [(III)]:

wherein,
$R^1$ and $R^2$ are each independently hydrogen or an organic group;
and the amino acid molecule is an amino acid, a linear peptide or a salt of the foregoing.

BRIEF DESCRIPTION OF THE FIGURES

These and other features of the preferred embodiments of the invention will become more apparent in the following detailed description in which reference is made to the appended drawings wherein.

DETAILED DESCRIPTION

Figure 1:
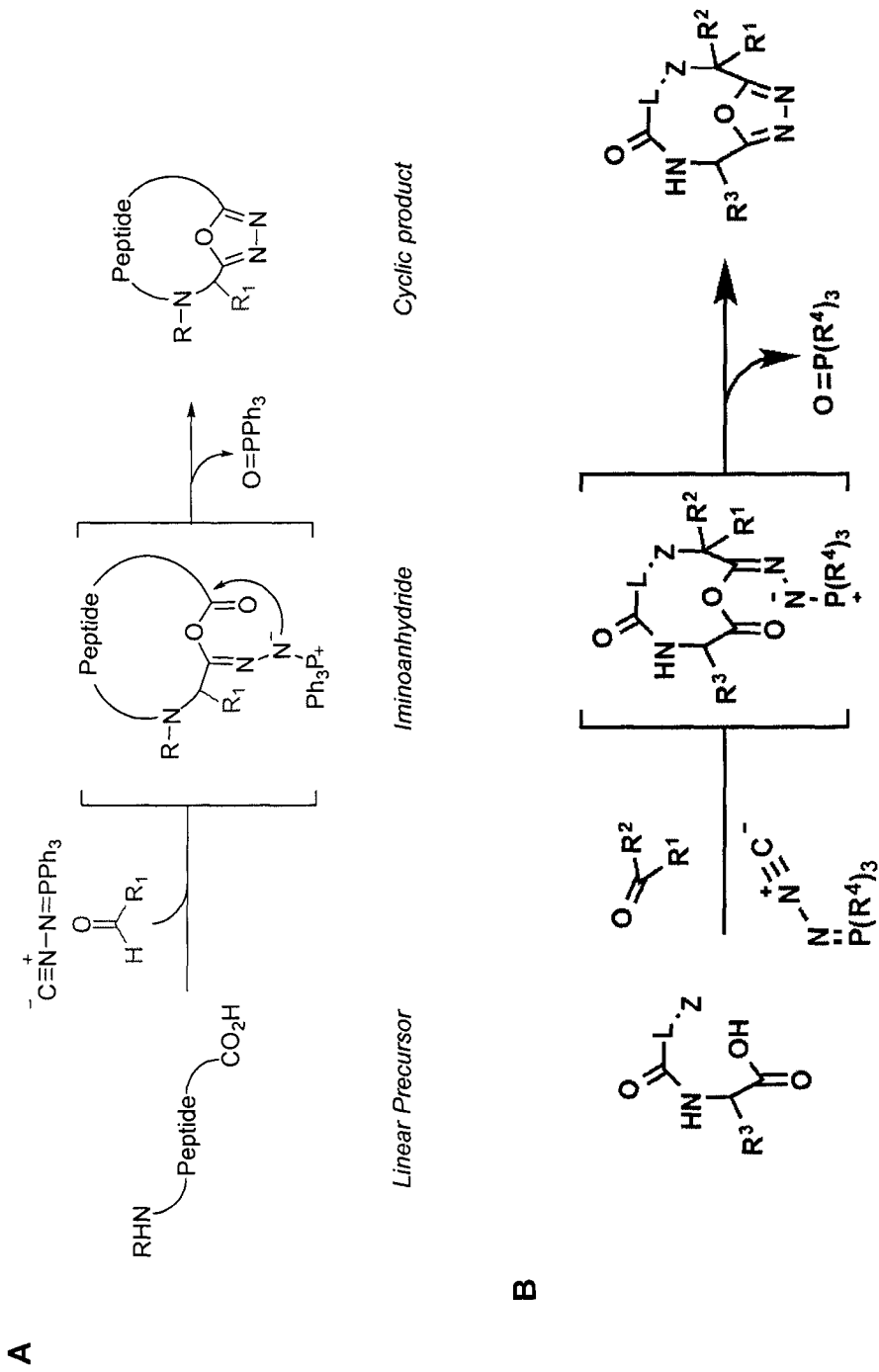
FIG. 1 shows (A) a schematic of the synthesis of 1,3,4-oxadiazole containing cyclic peptides and (B) a schematic of an alternative depiction of the synthesis of 1,3,4-oxadiazole containing cyclic peptides. Z is an amino terminus of an amino acid molecule; HO—C═O is a carboxy terminus of an amino acid; R1 and R2 are each independently hydrogen or an organic group; and R3 is equivalent to an amino acid side-chain.

In the following description, numerous specific details are set forth to provide a thorough understanding of the invention. However, it is understood that the invention may be practiced without these specific details.

In an embodiment, there is disclosed a cyclic molecule of formula [(I)]:

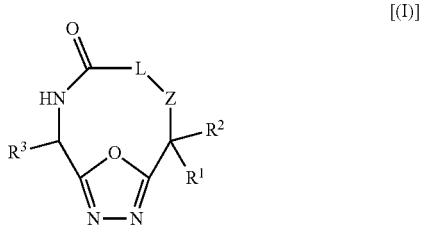

wherein,
Z is an amino terminus of an amino acid;
—C=O— is a carboxy terminus of an amino acid;
L, along with Z and —C=O— is an amino acid molecule;
$R^1$ and $R^2$ are each independently hydrogen or an organic group;
$R^3$ is equivalent to an amino acid side-chain; and
the amino acid molecule is an amino acid, a linear peptide or a salt of the foregoing.

In some embodiments, $R^1$ and $R^2$ are each independently selected from the group consisting of hydrogen, an alkyl group, a heteroalkyl group, a cycloalkyl group, an alkenyl group, a heteroalkenyl group, an alkynyl group, a heteroalkynyl group, an aryl group, a heteroaryl group, a heterocyclic group, an acyl group, an α-MIDA borylaldehyde, $CF_3$, $CH_2$—$CF_3$, a macrocycle, a fluorophore, an orthogonal reactive group, an affinity tag, an isotopically labeled molecule, a nucleoside, a nucleotide, a lipid, a carbohydrate, a small molecule, a functionalized solid support and a biologic.

As used herein, the term "amino acid molecule" is meant to include single amino acids and also peptides.

As used herein, the term "amino acid" refers to molecules containing an amine group, a carboxylic acid group and a side chain that varies. Amino acid is meant to include not only the twenty amino acids commonly found in proteins but also non-standard amino acids and unnatural amino acid derivatives known to those of skill in the art, and therefore includes, but is not limited to, alpha, beta, gamma and delta amino acids. Peptides are polymers of at least two amino acids and may include standard, non-standard, and unnatural amino acids.

Although in certain embodiments, cyclization of peptides are described, a person skilled in the art would understand based on the present description that the described methods could also be applied to cyclize a single amino acid.

In some embodiments, the organic group is substituted with one or more halide, hydroxyl, alkoxyl, acyloxyl or acyl groups.

The term "alkyl group" means a group formed by removing a hydrogen from a carbon of an alkane, where an alkane is an acyclic or cyclic compound consisting entirely of hydrogen atoms and saturated carbon atoms. An alkyl group may include one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "heteroalkenyl group" means a group formed by removing a hydrogen from a carbon of a heteroalkene, where a heteroalkene is an acyclic or cyclic compound consisting entirely of hydrogen atoms, carbon atoms and one or more heteroatoms, and including at least one carbon-carbon double bond. A heteroalkenyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "heteroalkynyl group" means a group formed by removing a hydrogen from a carbon of a heteroalkyne, where a heteroalkyne is an acyclic or cyclic compound consisting entirely of hydrogen atoms, carbon atoms and one or more heteroatoms, and including at least one carbon-carbon triple bond. A heteroalkynyl group may include one or more substituent groups.

The term "aryl group" means a group formed by removing a hydrogen from a ring carbon atom of an aromatic hydrocarbon. An aryl group may by monocyclic or polycyclic and may include one or more substituent groups.

The term "heteroaryl group" means a group formed by replacing one or more methine (—C=) and/or vinylene (—CH=CH—) groups in an aryl group with a trivalent or divalent heteroatom, respectively. A heteroaryl group may by monocyclic or polycyclic and may include one or more substituent groups.

The term "substituent group" means a group that replaces one or more hydrogen atoms in a molecular entity.

The term "heterocyclic group" means a group formed by removing a hydrogen from a cyclic compound that has atoms of at least two different elements as members of its ring(s).

The term "acyl group" means a group formed by removing one or more hydroxyl groups from an oxoacid, i.e. RCO—.

The term "hydroxyl group" means the group containing an oxygen atom connected by a covalent bond to a hydrogen atom, i.e. OH—.

The term "alkoxy group" means an alkyl group singularly bonded to oxygen, i.e. R—O.

In yet other embodiments, $R^1$ and $R^2$ are each independently selected from the group consisting of ethyl, benzyl and phenyl.

In some aspects, the α-MIDA borylaldehyde is $C_6H_9BNO_4$.

In some embodiments, the orthogonal reactive group is selected from the group consisting of a cyclic alkyne, a linear alkyne, a cyclic azide, a linear azide, a cyclic tetrazole and a linear tetrazole.

In yet other embodiments, the affinity tag is biotin.

In other embodiments, the biologic is selected from the group consisting of a functionalized peptide, protein, or amino acid.

In further embodiments, the functionalized solid support is a solid surface or resin bead.

In yet other embodiments, the small molecule is a drug.

In some embodiments, the cyclic amino acid is a lariat type macrocycle.

In still other embodiments, $R^1$ and $R^2$ are covalently linked to each other. In an aspect, $R^1$ and $R^2$ form cyclopentanone or other cycloalkanone.

In other embodiments, the amino terminus of the amino acid molecule is a primary amino group.

In yet other embodiments, the amino terminus of the amino acid molecule is a secondary amino group.

the amino acid molecule comprises a D or L amino acid.

In some embodiments, the amino acid molecule comprises an alpha-amino acid.

In other embodiments, the amino acid molecule comprises a beta-amino acid.

In still other embodiments, the amino acid molecule comprises a gamma-amino acid.

In some embodiments, the cyclic amino acid comprises a diastereomer at the carbon atom proximal to the aldehyde group.

In an aspect, the diastereomer is an (S) diastereomer.

In another aspect, the diastereomer is an (R) diastereomer.

In an embodiment, the peptide comprises at least 2 amino acids.

In another embodiment, there is disclosed a process to produce a cyclic amino acid molecule comprising reacting an amino acid molecule, having an amino terminus and a carboxyl terminus, with an isocyano-iminophosphorane having the formula (II):

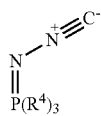

(II)

and a compound having the formula (III):

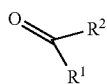

(III)

wherein,
$R^1$ and $R^2$ are each independently hydrogen or an organic group;
and the amino acid molecule is an amino acid, a peptide or a salt of the foregoing.

In some embodiments, $R^4$ is Ph. In other embodiments, $R^4$ is selected from the group consisting of an alkyl, an aryl and an alkoxy.

In some embodiments, the process further comprises conjugating a fluorescent tag to the cyclic molecule.

In some embodiments, the process further comprises deprotecting one or more side chains of the cyclic amino acid molecule if one or more of said side chains are protected with protecting groups.

The advantages of the present invention are further illustrated by the following examples.

The examples and their particular details set forth herein are presented for illustration only and should not be construed as a limitation on the claims of the present invention.

EXAMPLES

Materials and Methods

General Information:

Dichloroethane (DCE) was of reagent grade quality and Acetonitrile (MeCN) was HPLC grade. Linear peptide precursors were synthesized by Fmoc solid-phase-based peptide synthesis using 2-chlorotrityl chloride resin and double coupling steps with HBTU. Amino acid reagents were sourced from AAPPTec LLC, Louisville, Ky., USA and P3 BioSystems, LLC, Shelbyville, Ky., USA. Peptide grade DIPEA was sourced from Sigma Aldrich (Oakville, ON). Peptide grade NMP and DMF were sourced from Caledon Laboratories Ltd., Georgetown, Ontario, Canada. (N-isocyanimino)triphenylphosphorane was synthesized according to literature procedure described by Bio et. al.[27]

Nuclear Magnetic Resonance Spectra:

$^1H$ and $^{13}C$ NMR spectra were recorded Agilent 500 MHz, 600 MHz, and 700 MHz spectrometers. $^1H$ NMR spectra were referenced to DMSO-$d_6$ (δ 2.50 ppm).$^{13}C$ NMR spectra were referenced to DMSO-$d_6$ (δ 39.52 ppm). Peak multiplicities are designated by the following abbreviations: s, singlet; bs, broad singlet; d, doublet; t, triplet; q, quartet; m, multiplet; ds, doublet of singlets; dd, doublet of doublets; dt, doublet of triplets; ddd, doublet of doublet of doublets; bt, broad triplet; td, triplet of doublets; tdd, triplet of doublets of doublets.

Mass Spectrometry:

High-resolution mass spectra were obtained on a VG 70-250S (double focusing) mass spectrometer at 70 eV on a QStar XL (AB Sciex, Concord, ON, Canada) mass spectrometer with electrospray ionization (ESI) source, MS/MS and accurate mass capabilities. Alternatively, a JEOL AccuTOF model JMS-T1000LC mass spectrometer equipped with a Direct Analysis in Real Time (DART) ion source was used to acquire high-resolution mass spectra.

LC/MS:

Low-resolution mass spectra (ESI) were collected on an HPLC paired to a single-quad mass spectrometer. Compounds were resolved on an Agilent Poroshell 120 EC-$C_{18}$, 2.7 μm, 4.6×50 mm² column at room temperature with a flow of 1 mL/min. The gradient consisted of elutents A (0.1% formic acid in double distilled water) and B (0.1% formic acid in HPLC-grade acetonitrile). Absorbance was monitored at λ=214 nm.

LC/MS Method A:

The gradient method started at 5% of B for the first 1.0 minutes, followed by a linear gradient from 5% to 95% B in 15 minutes. The column was then washed with 95% B for 1.0 minutes and re-equilibrated at 5% B for 2 minutes.

LC/MS Method B:

The gradient method started at 5% of B and increased from 5% to 95% B in 4.0 minutes. The column was then washed with 95% B for 1.0 minutes and re-equilibrated at 5% B for 1.5 minutes.

General Cyclization and Deprotection Procedure:

In a oven dried 1 dram vial equipped with a magnetic stir bar, the linear peptide (0.05 mmol, 1 eq) was suspended in a 1:1 mixture of Dichloroethane and Acetonitrile (DCE: MeCN, 2.0 mL). Due to limited the solubility of the linear peptide the heterogeneous solution was sonicated to form a viscous homogeneous suspension. Aldehyde (0.075 mmol, 1.5 eq) was added to the suspension followed by (N-isocyanimino)triphenylphosphorane (0.05 mmol, 1 eq). The solution was stirred for 12 h at 50° C. Following completion of the reaction as monitored by LCMS the reaction mixture was dried under reduced pressure via rotary evaporation. The protected peptides were resuspended in 2.0 mL of deprotection solution (95% Trifluoroacetic Acid+2.5% $H_2O$+2.5% Triethylsilane) and stirred gently for 1 hour then the solvent was removed using a stream of $N_2$ then under reduced pressure.

RP-HPLC Separation:

The crude mixture from the side chain deprotection was resuspended in 3.0 mL of 1:1 $H_2O$:MeCN then resolved on a Biotage SNAP® cartridge (KP-C18-HS) 30 g column on a Teledyne ISCO Combiflash® Rf 200 at room temperature with a flow of 30 mL/min. The gradient consisted of eluents A (0.1% formic acid in double distilled water) and B (0.1% formic acid in HPLC-grade acetonitrile). The gradient method started at 10% of B for the first 3.0 minutes, followed by a linear gradient from 10% to 65% B in 22 minutes, then a linear gradient from 65% to 100% B in 3 minutes. The column was then washed with 100% B for 5.0 minutes and equilibrated at 10% B for 2 minutes. Fractions containing the target macrocycle were combined and lyophilized to afford the pure peptides as white powders.

Similar characterizations and structure confirmations were performed for all of the below compounds. The HPLC and spectra data are not shown in this specification for brevity.

Results and Discussion

Over the years, we have sought alternative multicomponent macrocyclization strategies that would place an intercepting nucleophile in the vicinity of a mixed anhydride. However, it was difficult to think of an amine other than aziridine that would be stable in the presence of the other macrocyclization components, in particular the aldehyde functionality. As part of a search for nucleophilic "interceptors", we recently came across isocyano-iminophosphoranes (ICIPs) as bench-stable reagents that incorporate both a nucleophillic amino group and an isocyanide into a single species.[11-12] These reagents have previously been applied for the synthesis of substituted 1,3,4-oxadiazoles via a one-pot multicomponent reaction.[13] Oxadiazoles have been a point of interest in medicinal chemistry as less polar proteolytically resistant isosteres of amide linkages.[14] We envisioned that ICIPs could also be applied in reactions with linear peptides to generate 1,3,4-oxadiazole containing peptide macrocycles, which we expected to exhibit unique conformational properties based on the rigid, planar, and de-peptidized nature of the oxadiazole linkage imbedded within the peptide backbone. Herein we report a broadly applicable multicomponent peptide macrocyclization reaction, mediated by isocyano-iminophosphoranes (ICIPs), to rapidly assemble structurally and functionally diverse 1,3,4-oxadiazole containing macrocyclic peptides of varying ring size and amino acid composition. (FIG. 1)

Preliminary Experiments

To investigate the feasibility of using ICIPs to generate oxadiazole containing macrocyclic peptides, we subjected the N-nucleophilic isocyanide, (N-isocyanimino)triphenylphosphorane, to a reaction with a model pentapeptide Pro-Gly-Leu-Gly-Phe (PGLGF), (1, Table 1) which has been well studied in the context of aziridine aldehyde mediated peptide cyclization. Propionaldehyde was chosen as the aldehyde component as it remains in solution at room temperature. After 3 h, at room temperature, a complete conversion of the linear precursor was observed and two isobaric species, in a 3:1 mixture, with masses corresponding to the target macrocycle were identified by LCMS analysis.

Following completion of the macrocyclization reaction the two species were separated and isolated then subjected to a detailed NMR investigation, which confirmed the oxadiazole linkage in each case, and revealed that the species were diastereomers with alternative stereocenters at the position corresponding to the aldehyde carbonyl carbon. The major S-product and was isolated in 50% yield. The minor R-product was isolated in 18% yield for a combined isolated yield of 68%. Both species exhibited conformational homogeneity by NMR, implying that the products are well ordered and conformationally rigid.

Variable Amino Acid Sequences and Ring Sizes

To investigate the applicability of this method across a broad range of sequences we next turned our attention to collection of 10 pentapeptides with varying residues in the peptide backbone. (2-11, Table 1) This collection was projected to generate a series of 18 membered rings, which has been show to be the most prevalent ring size in macrocyclic natural products.[15] As the hydrophobicity of the linear precursors increased, due to the protecting groups, their solubility in the reaction solvent became very low. To remedy this issue the reactions were heated to 50° C., which provided sufficient solubility to conduct the reactions. In each case, cyclization of the linear polypeptide precursor in the presence of (N-isocyanimino)triphenylphosphorane and propionaldehyde afforded the desired macrocyclic product in protected form, as a single product, with high (>95%) conversion, as determined by LCMS analysis. The resulting macrocycles were deprotected without isolation and then subjected to reverse phase purification. As outlined in Table 1, isolated yields ranged between 4-70%, with an average isolated yield of 38%, which is acceptable range for this type of purification.

In addition, shorter and longer sequences of 4, 6, and 7 amino acid residues were tested and were found to also undergo efficient macrocyclization to generate15-, 21-, and 24-membered rings, respectively. (12-16, Table 2) It is important to note that over the course of these reactions no oligiomerization products were observed. All together these experiments demonstrate that this method is tolerant to a wide range of peptide lengths and amino acid substitutions.

N-Methylated Residues

Figure 2:
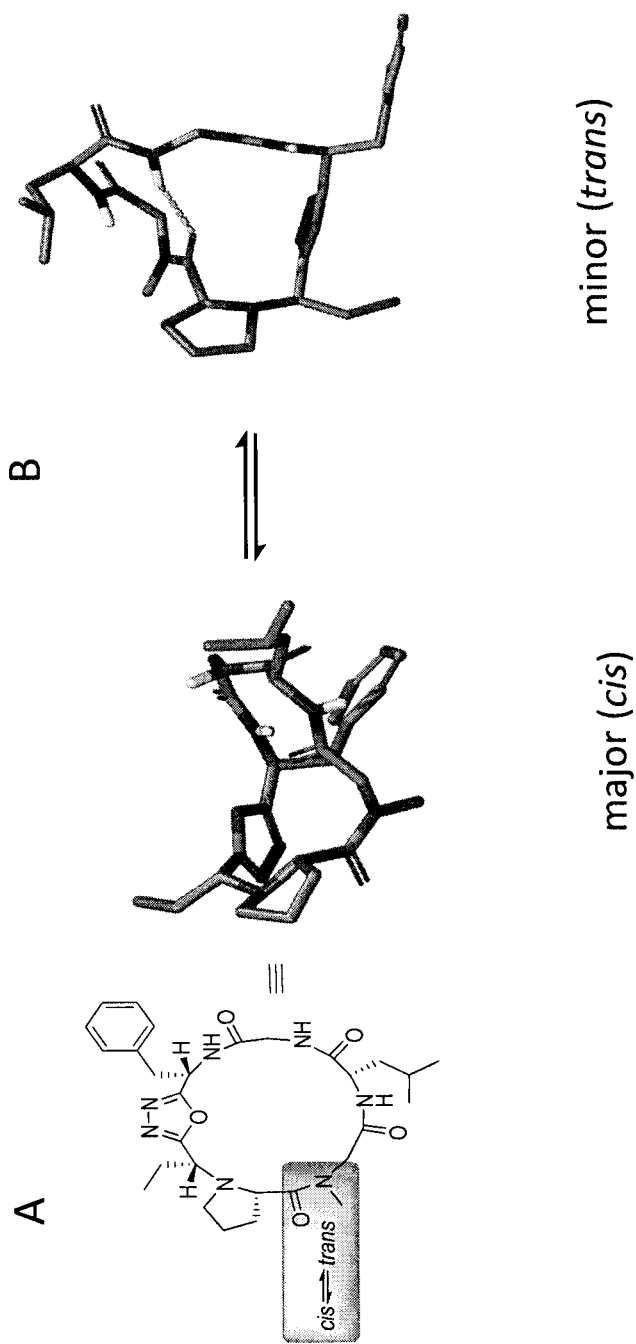
FIG. 2 shows NMR solution structures of compound 17 conformers (A) major conformer (B) minor conformer.

N-methylated amino acids are present in a number of biologically relevant cyclic-peptide natural products, perhaps most notably, in Cyclosporine A, a broad spectrum immunosupressant. The vast extent of N-methylation in cyclosporine A allows the macrocycle to undergo a conformational switching between inactive solution and active binding conformations via cis/trans isomerization of the amide bonds. In addition the conformational influences of N-methylation within synthetic peptides has been linked to increased membrane permeability,[16-17] enhanced metabolic stability,[18-20] heightened bioavailability,[21-22] and receptor selectivity.[23-24] Over methylation has, however, been shown to have deleterious effects.[25] To investigate the influence of N-methylation in the context of ICIP mediated cyclization, we referred back to the PGLGF model peptide and introduced a sarcosine residue in place of Glycine2 (sequence NH-Pro-Sar-Leu-Gly-Phe-$CO_2H$) (17, Table 3). Interestingly, when we isolated the major product of the macrocyclization reaction with propionaldehyde, we discovered that a 3:1 mixture of two species was present by $^1H$ NMR. EXSY experiments revealed that the two species were inter-converting conformers through selective irradiation and exchanged between the Phenylalanine α-protons of the major and minor species. The ROESY data, specifically the coupling between the Proline α-proton to Sarcosine α-protons for the two conformers, revealed that the major conformer had a cis-amide bond at the proline/sacrosine junction whereas the minor conformer exhibited all trans-amide bond geometry throughout the molecule. The NMR solution structure was solved for the major cis- and minor trans-conformers. As shown in FIG. 2, the major conformer (A) displays an unique boat-like geometry, while the minor conformer (B) displays a more conventional turn geometry. The 6-mer linear peptide NH-Pro-Sar-Leu-Gly-Phe-Ala-$CO_2H$ also cyclized readily via this approach (18, Table 3).

Variable Aldehydes and Ketones

During the method development and investigation of the preliminary macrocyclization scope, the aldehyde component, propionaldehyde, served only as a linker between the N-terminus and the oxadiazole. We envisioned that this aldehyde component could be leveraged to introduce important functionalities into the peptide backbone. First, we envisioned varying the aldehyde to mimic the side chain of an amino acid, which could be used to actively engage a target or influence the conformational properties of the resulting macrocycles. To this end, we employed phenylacetaldehyde, which would correspond to a phenylalanine side chain and isovaleraldehyde, which would correspond to a leucine side chain. Reaction of the peptides Pro-Ser(OtBu)-Trp(Boc)-Ala-Gly, Pro-Ser(OtBu)-Leu-Tyr(OtBu)-Gly, and Pro-Gly-Leu-Gly-Phe with phenylacetaldehyde afforded the target macrocycles in yields comparable to the macrocycles formed with propionaldehyde. (19-21, Table 4). The peptide, Pro-Gly-Leu-Gly-Phe was also reacted in the presence of isovaleraldehyde to demonstrate that a single sequence can be successfully cyclized in the presence of multiple aldeydes (22, Table 4).

In order to facilitate rapid post cyclization derivatization, we also utilized an α-MIDA borylaldehyde in the cyclization reaction with PSarLFG.[26] (23, Table 2) The protected boronic acid could serve as a chemical handle for rapid combinatorial post cyclization derivatization via transition metal mediated cross coupling. In addition, boronic acids have recently become of interest as modulators of cellular permeability. This methodology therefore affords us the opportunity to rapidly modulate the composition and functionality of the macrocyclic products by varying the nature of the aldehyde prior to cyclization, or the coupling partner, post cyclization. It is attractive to envision also introducing alternative biologically relevant functional groups such as fluorophores or affinity tags to aid in screening peptide ligands.

Ketones could also be utilized in the cyclization reaction. As shown in Table 5, both acetone and cyclohexanone could be employed in the (N-isocyanimino)triphenylphosphorane mediated cyclization of 5-mer peptides based on the Pro-Phe-Leu-Asp-Ala sequence, affording oxadiazole-containing macrocycles that are not formed as a mixture of diastereomers (24-25, Table 5).

Primary N-Terminal Residues

In addition to proline terminated peptides we were also interested in applying the present method for the cyclization of peptides with a primary N-terminus and for peptides containing no proline residues, substrate classes that remained unreactive in aziridine aldehyde mediated cyclization. We investigated the reactivity of several varied 4-mer and 5-mer sequences with different aldehyde components, namely propionaldehyde, phenylacetaldehyde, and benzaldehyde. (26-34, Table 6). Each substrate and aldehyde reacted successfully in the presence of (N-isocyanimino) triphenylphosphorane to generate the desired macrocyclic products with isolated yields ranging from 15-70%. These reactions demonstrate the opportunity to rapidly modulate the product composition by varying the nature of the peptidic and aldehyde component and reveal that proline or other turn inducing residues are not required to achieve macrocyclization.

Mechanistic Discussion

Figure 3:
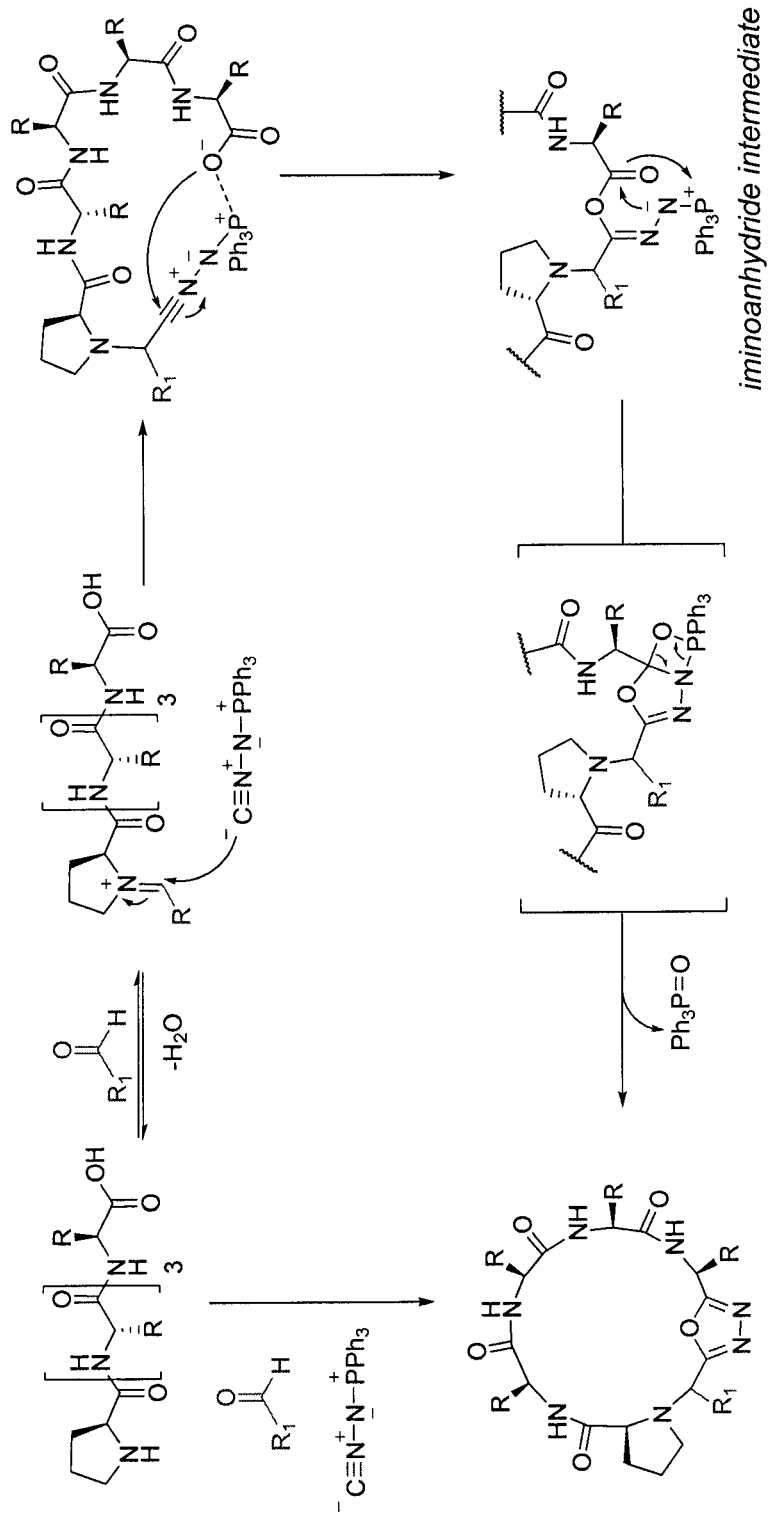
FIG. 3 shows a proposed mechanism for (N-isocyan-imino)triphenylphosphorane mediated multicomponent peptide cyclization.

The macrocyclization reaction is proposed to go through a stepwise process starting with condensation of the aldehyde with the peptide N-terminus to form an iminium intermediate, which is then intercepted via addition of the isocyanide, setting a stereocenter in the final products. Macrolactonization of the isonitrilium intermediate by the peptide C-terminus results in the formation of an imino-anhydride intermediate. Finally, the exocyclic imino phosphorane, which is only 3 atoms away from iminoanhydride, coordinates an aza-Wittig type reaction, via a favorable 5 membered transition state, to generate the 1,3,4-oxadiazole linkage. (FIG. 3) The success of this reaction, and the lack of detectable oligomerization products at relatively high concentrations (25-100 mM depending on peptide solubility), is likely a manifestation of zwitterionic control over cyclization efficiency, which was also operative in the aziridine aldehyde-based process. Our proposal is that within the isonitrillium intermediate the positively charged triphenylphosphonium ion of the iminophosphorane accounts for the attractive electrostatic interaction with the negatively charged carboxylate ion, ultimately leading to the efficient formation of the iminoanhydride intermediate, and finally the macrocyclic product.

Hydrogen Bonding in 1,3,4-Oxadiazole Containing Macrocycles

Figure 4:
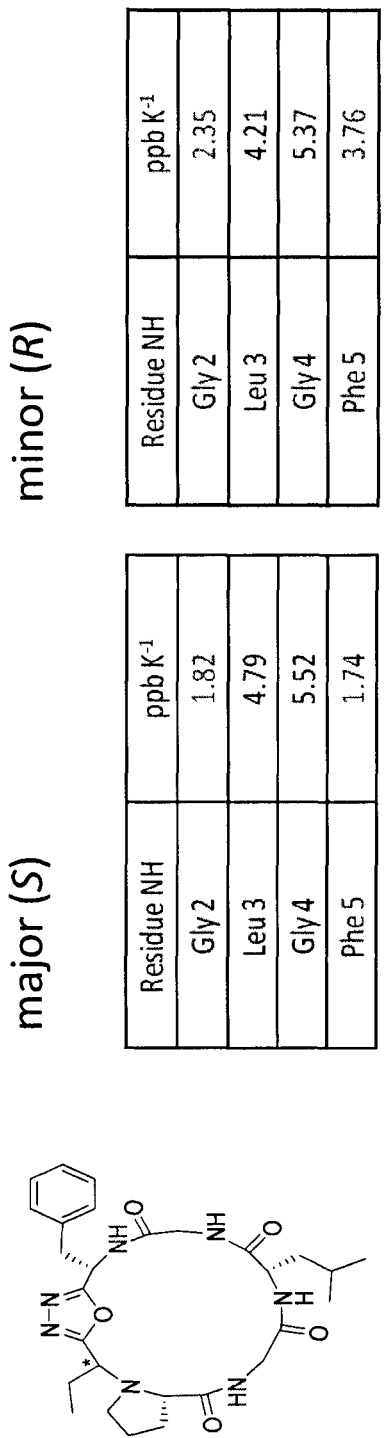
FIG. 4 shows hydrogen bonding within cyclo[PGLGF] odz/ethyl diastereomers (Compound 1). Hydrogen atoms that participate are highlighted in red. The diastereomeric aldehyde center is highlighted with an asterisk.
Figure 5:
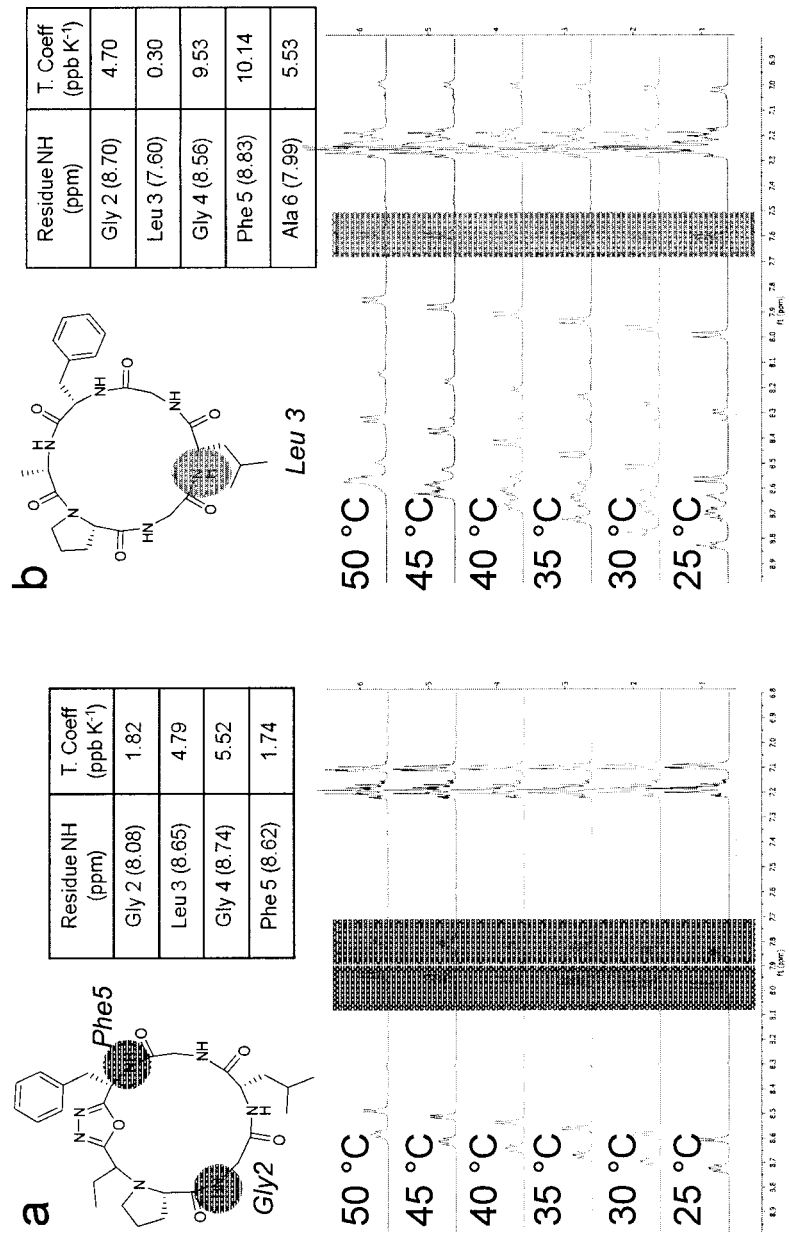
FIG. 5 shows the hydrogen bonding profile and temperature shift coefficients (T. Coeff) of a, oxadiazole and b, homodetic peptide macrocycles, based on the PGLGF sequence, as measured by variable temperature $^1$H NMR. Hydrogen atoms engaged in intramolecular hydrogen bonding and their corresponding NMR signals are highlighted. The oxadiazole-containing macrocycle exhibits an alternative hydrogen bonding pattern and displays increased conformational rigidity as compared to the homodetic variant.

Variable temperature NMR was used to probe the hydrogen bonding patterns exhibited by 1,3,4-oxadiazole containing peptides synthesized via this approach. First, the hydrogen bonding within both diastereomers of Compound 1 (cyclo[PGLF]/propionaldehyde) in $D_6$-DMSO was investigated using variable temperature $^1H$ NMR (25-55° C.). As shown in FIG. 4, both diastereomers exhibited identical hydrogen patterns (H-bonds are defined by a ppb $K^{-1}$ below 4) suggesting that the aldehyde derived stereo-center does not significantly influence the overall conformational geometry of the macrocyclic products. Based on these experiments it was concluded that the Gly2 and Phe5 NHs participate in hydrogen bonding, while the Leu3 and Gly4 NHs do not. The hydrogen bonding pattern of the Compound 1 major disatereomer was also compared to an analogous 18 membered homodetic macrocycle based on the PGLGF sequence (FIG. 5). The variable temperature $^1H$-NMR spectra and temperature shift coefficients show two major differences. First, the oxadiazole-containing macrocycle displays an alternative hydrogen bonding pattern as compared to its homodetic counterpart. Second, the oxadiazole-containing macrocycle (Compound 1) exists as a single conformer in solution while the homodetic macrocycle exists as a mixture of conformers at all temperatures.

Figure 6:
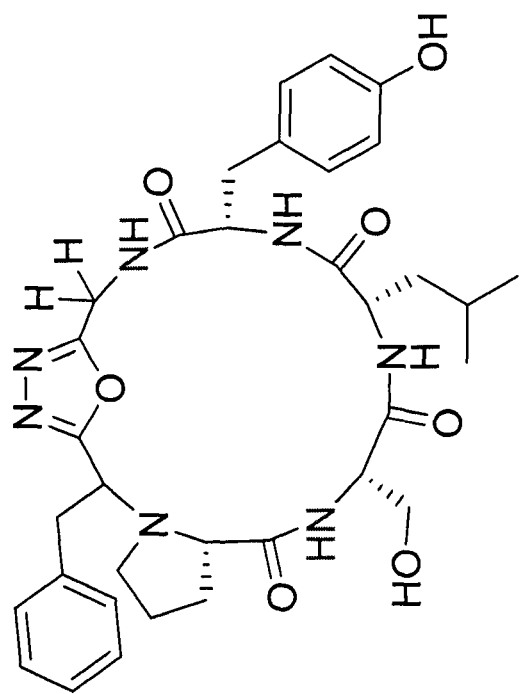
FIG. 6 shows hydrogen bonding within Compound 20 (cyclo[PSLYG]odz/benzyl) major diastereomer. Hydrogen atoms that participate are highlighted in red.
Figure 7:
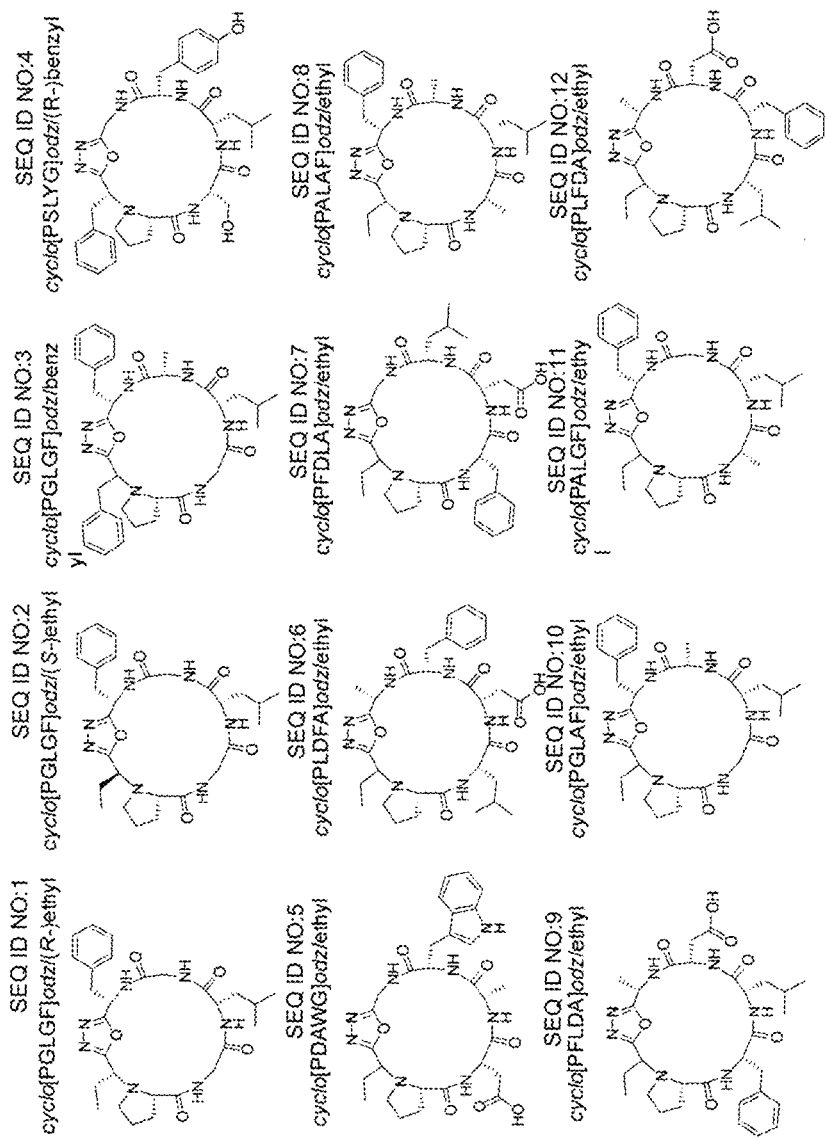
FIG. 7 shows SEQ ID NOs: 1-12.

In addition to Compound 1 we also investigated the H-bonding pattern exhibited by several other macrocycles. Compound 20, (cyclo[PSLYG]/phenylacetaldehyde) an 18 membered oxadiazole containing macrocycle comprised of different amino acid residues and a different aldehyde component than Compound 1. Importantly, as shown in FIG. 6, Compound 20 displays the same hydrogen bonding pattern, more specifically at the residues in positions 2 and 5. This result suggested that the proline-aldehyde-oxadiazole linkage can serve as a robust turn stabilizing motif regardless of the aldehyde component or peptide sequence composition. To further investigate the generality of this hydrogen bonding pattern we also defined the intramolecular hydrogen bonding patterns of several other macrocycles using the same variable temperature NMR experiments (FIG. 7). Importantly, all oxadiazole-containing 18 membered rings showed the same 2,5-hydrogen bonding pattern. In some cases additional hydrogen bonds were also observed.

Structural Characteristics and Turn Inducing Elements

Figure 8:
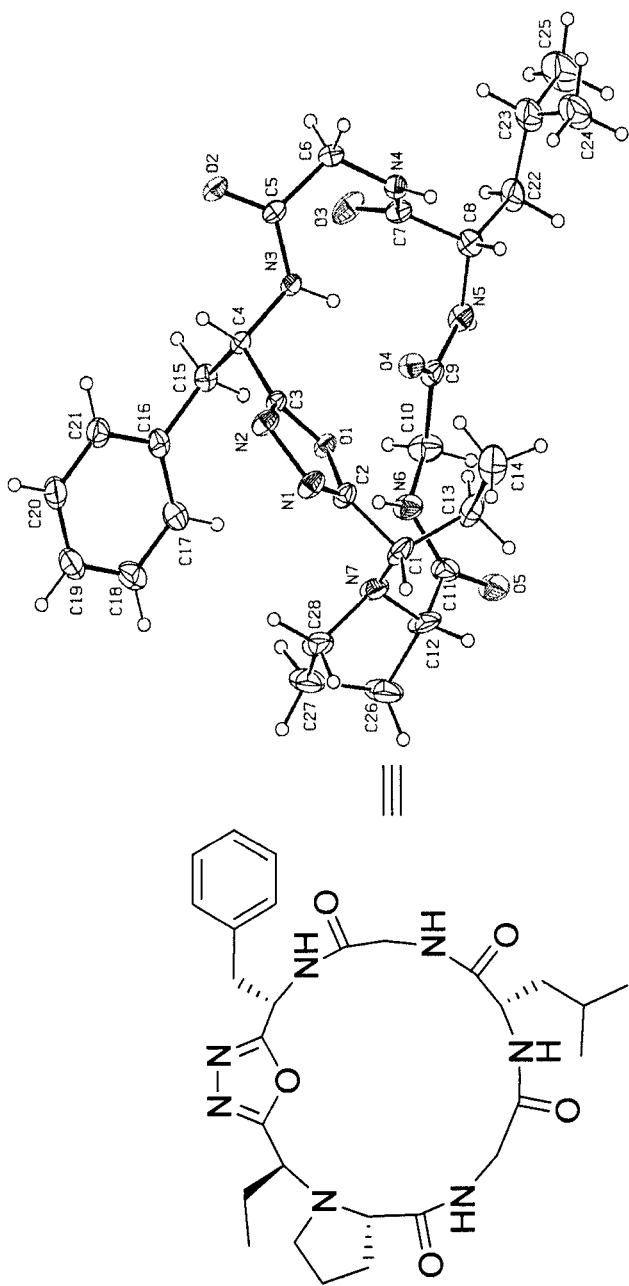
FIG. 8 shows Crystallographic Data for cyclo[PGLGF] odz/ethyl (1).
Figure 9:
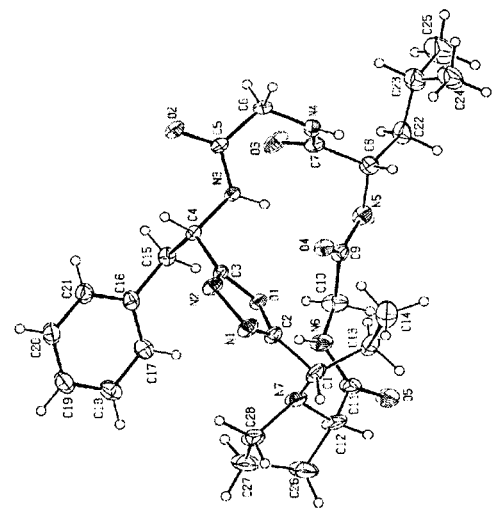
FIG. 9 shows the structural analysis of Compound 1, cyclo[PGLGF]odz/ethyl S-diastereomer (a) X-ray crystal structure and (b) overlay of NMR solution structure in $D_6$-DMSO (green) with crystal structure (grey).
Figure 9:
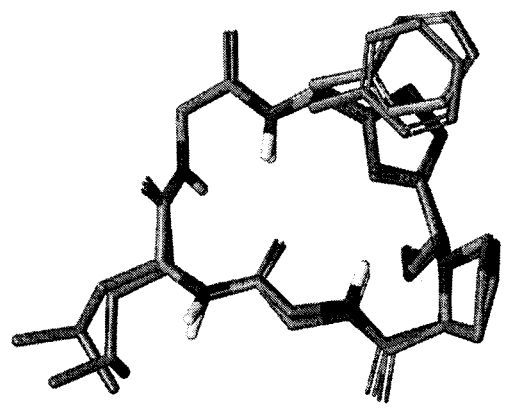

The X-ray crystal structure was solved for the major (S−) diastereomer of Compound 1 (FIG. 8). The crystal structure supports the outlined H-bonding pattern described above (FIG. 9A). Both the tertiary proline derived amino group and the oxadiazole oxygen are with appropriate distance (<3 Å) from the Gly2 NH to serve as H-bonding acceptors. Also, the Gly2 Carbonyl is appropriately positioned to engage the Phe5 NH. By overlaying the modeled NMR solution structure of Compound 1 with the obtained crystal structure reveals a remarkable similarity between the two, thereby highlighting the conformational homogeneity and structural rigidity exhibited by oxadiazole containing macrocycles in solution. (FIG. 9B) Most importantly, the Leu3 and Gly4 ψ/φ angles (=$\psi_1$ −64°, $\psi_2$ 86°, $\phi_1$ 113°, $\phi_2$ 8°) obtained from the X-ray crystal structure match very closely with the theoretical angles for a Type II β-turn (=$\psi_1$ −60°, $\psi_2$ 80°, $\phi_1$ 120°, $\phi_2$ 0°), the most prevalent turn structure in biologically active peptides. This observation suggests that the outlined methodology can be utilized to stabilize biologically relevant secondary structures in macrocyclic peptides.

Passive Membrane Permeability of Oxadiazole-Containing Peptide Macrocycles

Figure 10:
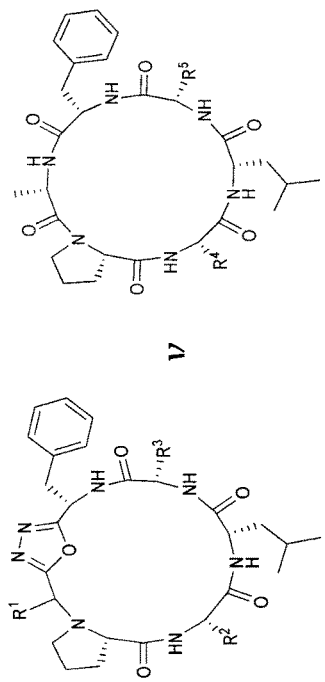
FIG. 10 shows measured PAMPA values ($-\log P_e$) and structure comparison of oxadiazole-containing and homodetic peptide macrocycles are provided. Differing connectivities are highlighted in blue.

Passive membrane permeability is an important property for the development of new therapeutics. A passive artificial membrane permeability (PAMPA) assay was utilized to measure the extent of passive membrane permeability displayed by oxadiazole-containing peptide macrocycles. Using this analysis method a −log $P_e$ value <6.0 is indicitive of a passively membrane permeable compound, while a −log $P_e$>6.0 is indicative of a poorly permeable or non-permeable compound. As shown in FIG. 10, a collection of oxadiazole-containing peptide macrocycles (entries 1-7) and their analogous homodetic counterparts (entries 8-12) were subjected to PAMPA analysis. Importantly, in all cases, the oxadiazole containing peptide macrocycles (entries 1-7, FIG. 10) were passively membrane permeable (evidenced by −log $P_e$ values <6.0) and displayed higher passive membrane permeability than their homodetic counterparts. In 4 out of 5 cases the homodetic macrocycles were not passively membrane permeable with the single exception being the highly hydrophobic cyclo[PFLLFA] (entry 12).

Conclusions

We have developed a robust approach to rapidly access structurally diverse macrocycle peptides via a multicomponent reaction. This method relies on the application of (N-isocyanimino)triphenylphosphorane, which places a pendant exocyclic amine in position to intercept an imino-anhydride intermediate. The resulting product is cyclic molecule with a 1,3,4-oxadiazole imbedded within the peptide backbone. By varying the length and composition of the peptidic component we were able to generate 15, 18, 21, and 24 membered rings using this approach. By varying the nature of the aldehyde component alternative functional groups were introduced into the macrocyclic products. N-methylation studies revealed an opportunity to generate macrocycles that undergo conformational exchange, via cis/trans amide isomerization, and exhibit unique structural properties. Variable temperature NMR investigations revealed a conserved H-bonding pattern than persists in 18 membered macrocyclic products independent of the peptide or aldehyde compositions. Overlay of the crystal structure and NMR solution structure revealed a highly conserved conformational geometry wherein the oxadiazole oxygen and tertiary N-terminal amino group may both contribute to the conformational stabilization by accepting hydrogen bonds, as observed in the X-ray crystal structure. A unique enabling feature of this approach involves the formation of a unprecedented motif in the form of a contiguous non-amidated N-terminal amino group, variable aldehyde, and 1,3,4-oxadiazole triad, which accommodates the formation of a stable Type I and Type II β-turns. β-turns are present in a number of biologically active peptides, supporting the application of this methodology for the development of new therapeutics and biological probes. Oxadiazole-containing macrocycles can display passive membrane permeability and therefore represent attractive candidates for the development of new probes and therapeutics.

Compound Characterization

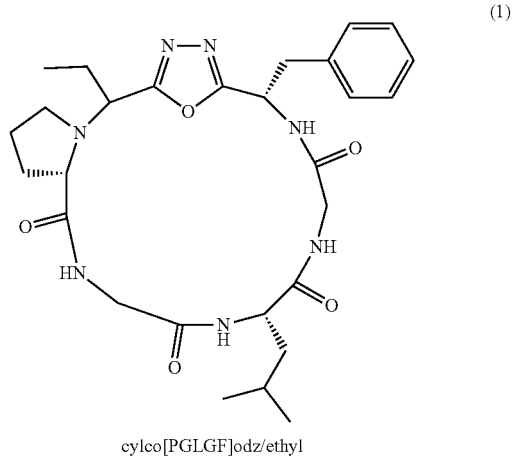 [SMILES: CCC1c2nnc(o2)[C@H](Cc2ccccc2)NC(=O)CNC(=O)[C@H](CC(C)C)NC(=O)CNC(=O)[C@@H]2CCCN12]

(1)

cylco[PGLGF]odz/ethyl

The peptide NH-Pro-Gly-Leu-Gly-Phe-CO$_2$H (24.5 mg, 0.05 mmol, 1 eq) was dissolved in a mixture of 1:1 Dichloroethane:Acetonitrile (1 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization and reverse phase purification the pure fractions were pooled and lyophilized to afford 14 mg of the title compound major diastereomer 1a (50% yield) and 5 mg of the minor diastereomer 1b (18% yield) for a total 68% overall yield.

Major (S,S)-1a: HR-MS (ESI) calculated for C$_{28}$H$_{40}$N$_7$O$_5$ [M+H]$^+$: 554.3085. found: 554.3086.

HPLC Method A: Retention Time 7.85 min

Minor (R,S)-1b: HR-MS (ESI) calculated for C$_{28}$H$_{40}$N$_7$O$_5$ [M+H]$^+$: 554.3085. found: 554.3083.

HPLC Method A: Retention Time 8.15 min

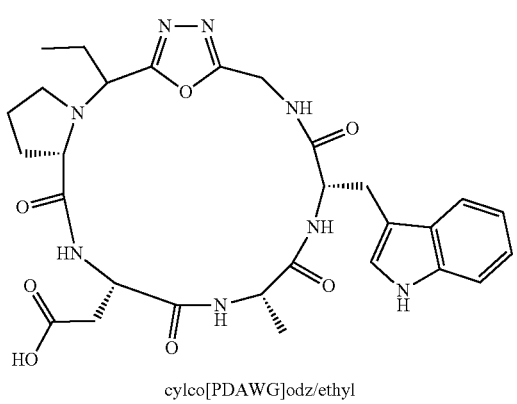

cylco[PDAWG]odz/ethyl

The peptide NH-Pro-Asp(O$^t$Bu)-Ala-Trp(Boc)-Gly-CO$_2$H (35 mg, 0.05 mmol, 1 eq) was dissolved in a mixture of 1:1 Dichloroethane:Acetonitrile (2 mL). Propionaldehyde (5.4 L, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 6.7 mg of the title compound in 22% overall yield as a 3.5:1 mixture of diastereomers.

HR-MS (ESI) calculated for C$_{29}$H$_{37}$N$_8$O$_7$ [M+H]$^+$: 609.278. found: 609.2791.

HPLC Method A:

Retention time (major diastereomer) 6.28 min

Retention time (minor diastereomer) 6.39 min

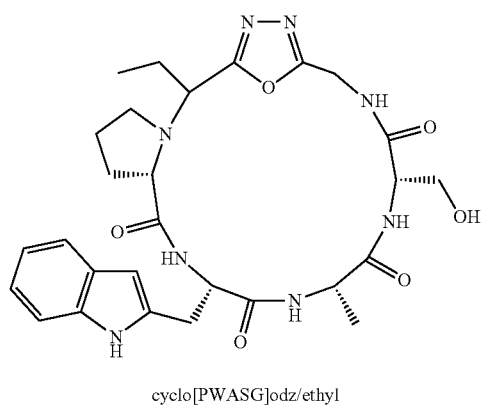

cyclo[PWASG]odz/ethyl

The peptide NH-Pro-Trp(Boc)-Ala-Ser(O$^t$Bu)-Gly-CO$_2$H (33.6 mg, 0.05 mmol, 1 eq) was dissolved in a mixture of 1:1 Dichloroethane:Acetonitrile (2 mL). Propionaldehyde (5.4 μL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 8.2 mg of the title compound in 28% overall yield as a 2.9:1 mixture of diastereomers.

HR-MS (ESI) calculated for C$_{28}$H$_{37}$N$_8$O$_6$ [M+H]$^+$: 581.2831. found: 581.2826.

HPLC Method A:

Retention time (major diastereomer) 6.80 min

Retention time (minor diastereomer) 6.91 min

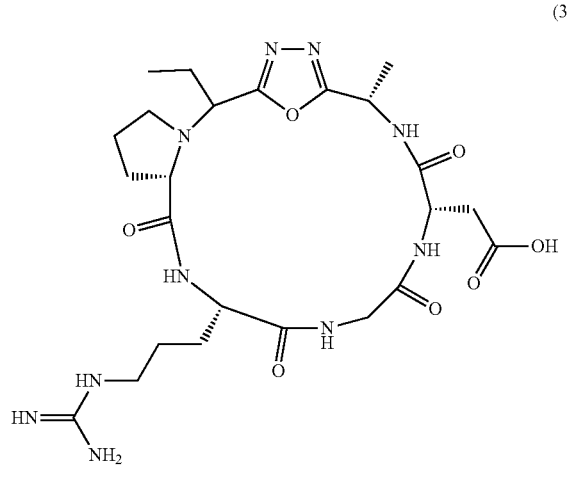

cylco[PRGDA]odz/ethyl

The peptide NH-Pro-Arg(Pbf)-Gly-Asp(OtBu)-Ala-CO$_2$H was cyclized at 0.05 mmol scale with propionaldehyde (1.5 eq) and (N-isocyanimino)triphenylphosphorane (1 eq). After cyclization, deprotection, and reverse phase purification the pure fractions were pooled and lyophilized to afford 20.2 mg of the title compound in 70% overall yield.

HR-MS (ESI) calculated for C$_{24}$H$_{39}$N$_{10}$O$_7$ [M+H]$^+$: 579.2998. found: 579.3006.

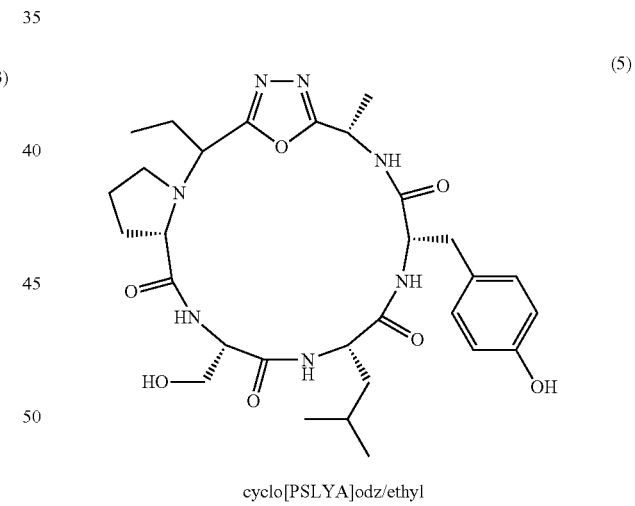

cyclo[PSLYA]odz/ethyl

The peptide NH-Pro-Ser(O$^t$Bu)-Leu-Tyr(O$^t$Bu)-Ala-CO$_2$H (33.1 mg, 0.05 mmol, 1 eq) was dissolved in a mixture of 1:1 Dichloroethane:Acetonitrile (2 mL). Propionaldehyde (5.4 μL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 7.4 mg of the title compound in 24% overall yield as a 3:1 mixture of diastereomers.

HR-MS (ESI) calculated for C$_{30}$H$_{44}$N$_7$O$_7$ [M+H]$^+$: 614.3297. found: 614.3312.

HPLC Method A:
Retention time (major diastereomer) 6.64 min
Retention time (minor diastereomer) 6.82 min

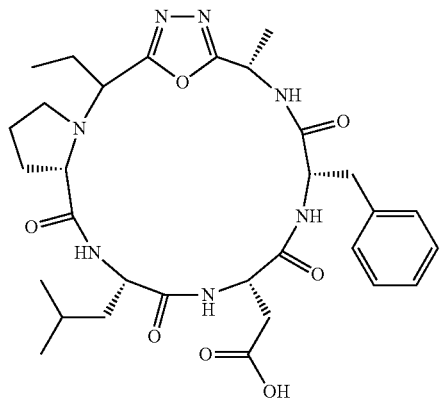

cyclo[PLDFA]odz/ethyl

The peptide NH-Pro-Leu-Asp(O$^t$Bu)-Phe-Ala-CO$_2$H (30.9 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 16.2 mg of the title compound in 52% overall yield as a single diastereomer.

HR-MS (ESI) calculated for $C_{31}H_{44}N_7O_7$ [M+H]$^+$: 626.3297. found: 626.3307.

HPLC Method A:
Retention time (major diastereomer) 8.32 min

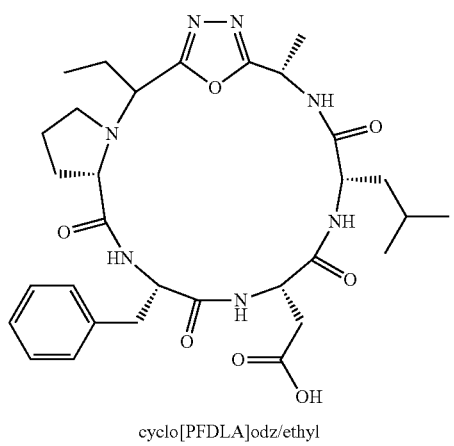

cyclo[PFDLA]odz/ethyl

The peptide NH-Pro-Phe-Asp(O$^t$Bu)-Leu-Ala-CO$_2$H (30.9 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 14 mg of the title compound in 45% overall yield as a 5.9:1 mixture of diastereomers.

HR-MS (ESI) calculated for $C_{31}H_{44}N_7O_7$ [M+H]$^+$: 626.3297. found: 626.3301.

HPLC Method A:
Retention time (major diastereomer) 8.21 min
Retention time (minor diastereomer) 8.29 min

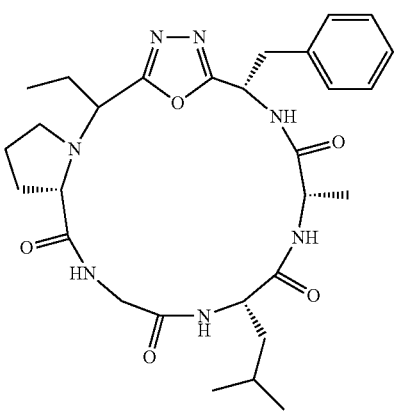

cyclo[PGLAF]odz/ethyl

The peptide NH-Pro-Gly-Leu-Ala-Phe-CO$_2$H (25.2 mg, 0.05 mmol, 1 eq) was dissolved in a mixture of 1:1 Dichloroethane:Acetonitrile (2.5 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 6.5 mg of the title compound in 23% overall yield as a 4.9:1 mixture of diastereomers.

HR-MS (ESI) calculated for $C_{29}H_{41}N_7O_5$ [M+H]$^+$: 568.3169. found: 568.3250.

HPLC Method A:
Retention time (major diastereomer) 8.05 min
Retention time (minor diastereomer) 8.21 min

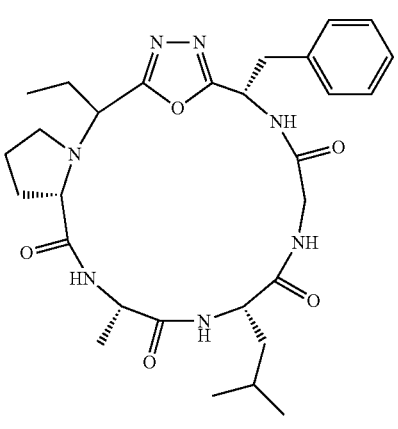

cyclo[PALGF]odz/ethyl

The peptide NH-Pro-Ala-Leu-Gly-Phe-CO$_2$H (25.2 mg, 0.05 mmol, 1 eq) was dissolved in a mixture of 1:1 Dichloroethane:Acetonitrile (2.5 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 7 mg of the title compound in 25% overall yield as a 1.8:1 mixture of diastereomers.

HR-MS (ESI) calculated for $C_{29}H_{41}N_7O_5$ $[M+H]^+$: 568.3169. found: 568.3242.

HPLC Method A:
Retention time (major diastereomer) 8.87 min
Retention time (minor diastereomer) 9.18 min

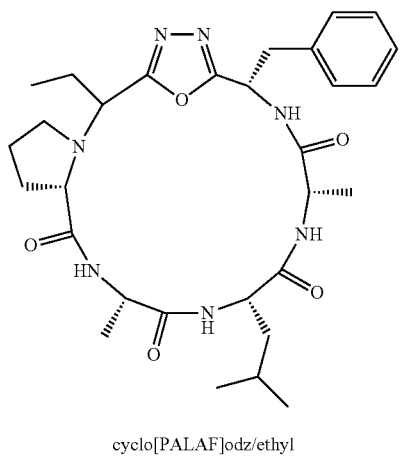

cyclo[PALAF]odz/ethyl

The peptide NH-Pro-Ala-Leu-Ala-Phe-CO$_2$H (25.9 mg, 0.05 mmol, 1 eq) was dissolved in a mixture of 1:1 Dichloroethane:Acetonitrile (2.5 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 5.9 mg of the title compound in 20% overall yield as a 3.4:1 mixture of diastereomers.

HR-MS (ESI) calculated for $C_{30}H_{43}N_7O_5$ $[M+H]^+$: 582.3326. found: 582.3381.

HPLC Method A:
Retention time (major diastereomer) 9.05 min
Retention time (minor diastereomer) 9.24 min

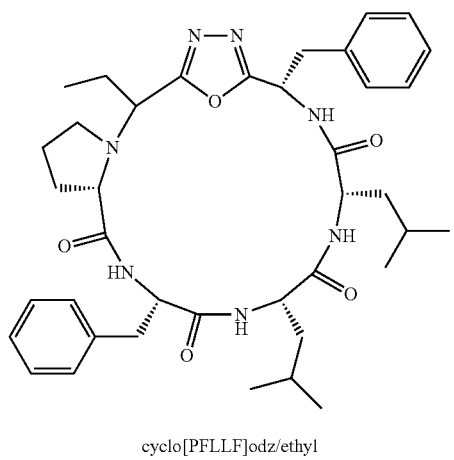

cyclo[PFLLF]odz/ethyl

The peptide NH-Pro-Phe-Leu-Leu-Phe-CO$_2$H (31.8 mg, 0.05 mmol, 1 eq) was dissolved in a mixture of 1:1 Dichloroethane:Acetonitrile (3 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 8.8 mg of the title compound in 25% overall yield as a 2.7:1 mixture of diastereomers.

HR-MS (ESI) calculated for $C_{39}H_{53}N_7O_5$ $[M+H]^+$: 700.4108. found: 700.4182.

HPLC Method A:
Retention time (major diastereomer) 11.71 min
Retention time (minor diastereomer) 11.90 min

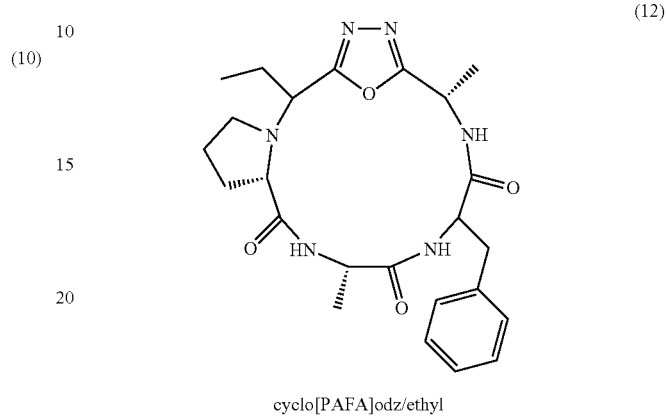

cyclo[PAFA]odz/ethyl

The peptide NH-Pro-Ala-Phe-Ala-CO$_2$H (20.2 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 5.4 mg of the title compound in 23% overall yield as a 5.2:1 mixture of diastereomers.

HR-MS (ESI) calculated for $C_{24}H_{32}N_6O_4$ $[M+H]^+$: 469.2485. found: 469.2544.

HPLC Method A:
Retention time (major diastereomer) 7.00 min
Retention time (minor diastereomer) 7.18 min

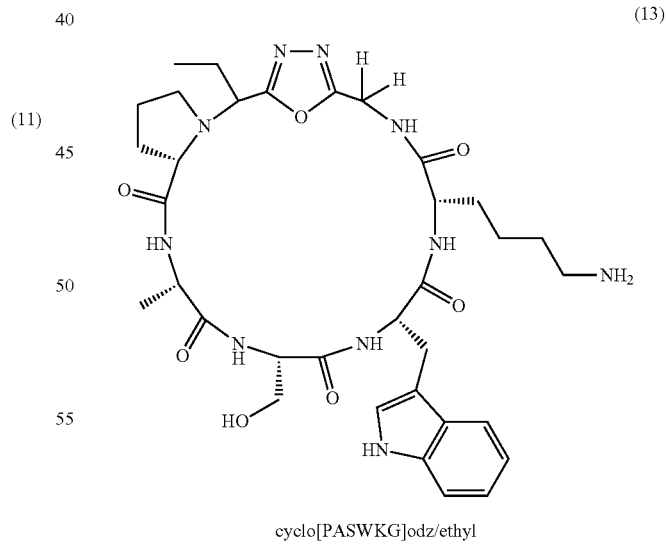

cyclo[PASWKG]odz/ethyl

The peptide NH-Pro-Asp(OtBu)-Ser(OtBu)-Trp(Boc)-Lys(Boc)-Gly-CO$_2$H was cyclized at 0.05 mmol scale with propionaldehyde (1.5 eq) and (N-isocyanimino)triphenylphosphorane (1 eq). After cyclization, deprotection, and reverse phase purification the pure fractions were pooled and lyophilized to afford 2.4 mg of the title compound in 7% overall yield.

HR-MS (ESI) calculated for $C_{34}H_{49}N_{10}O_7$ [M+H]$^+$: 709.3780. found: 709.3776.

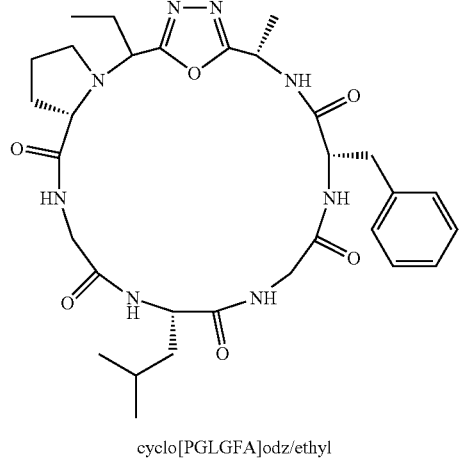

cyclo[PGLGFA]odz/ethyl (14)

The peptide NH-Pro-Gly-Leu-Gly-Phe-Ala-CO$_2$H (28 mg, 0.05 mmol, 1 eq) was dissolved in a mixture of 1:1 Dichloroethane:Acetonitrile (2 mL). Propionaldehyde (5.4 μL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 12.8 mg of the title compound in 41% overall yield as a single diastereomer.

HR-MS (ESI) calculated for $C_{31}H_{45}N_8O_6$ [M+H]$^+$: 625.3457. found: 625.3461.

HPLC Method A:
Retention time (major species) 6.85 min (15)

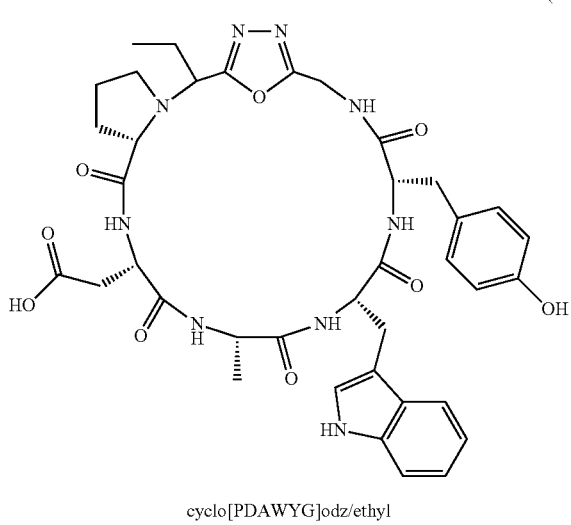

cyclo[PDAWYG]odz/ethyl

The peptide NH-Pro-Asp(O$^t$Bu)-Ala-Trp(Boc)-Tyr(O$^t$Bu)-Gly-CO$_2$H (46 mg, 0.05 mmol, 1 eq) was dissolved in a mixture of 1:1 Dichloroethane:Acetonitrile (2 mL). Propionaldehyde (5.4 μL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 10 mg of the title compound in 28% overall yield as a 6.4:1 mixture of diastereomers.

HR-MS (ESI) calculated for $C_{38}H_{46}N_9O_9$ [M+H]$^+$: 772.3413. found: 772.3411.

HPLC Method B:
Retention time (major diastereomer) 3.05 min
Retention time (minor diastereomer) 3.10 min (16)

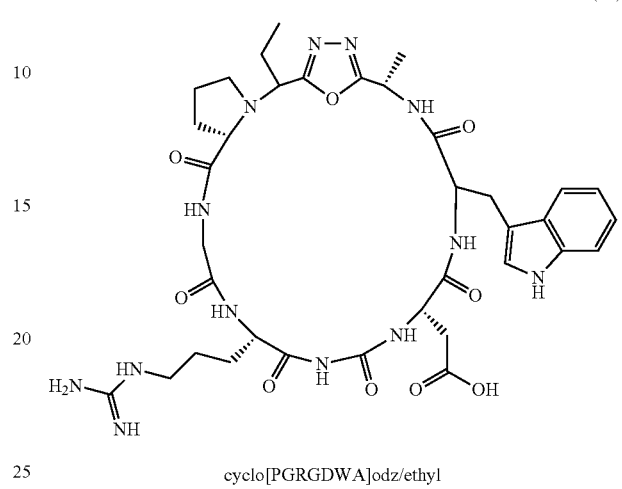

cyclo[PGRGDWA]odz/ethyl

The peptide NH-Pro-Gly-Arg(Pbf)-Gly-Asp(O$^t$Bu)-Trp(Boc)-Ala-CO$_2$H (58.3 mg, 0.05 mmol, 1 eq) was dissolved in a mixture of 1:1 Dichloroethane:Acetonitrile (2 mL). Propionaldehyde (5.4 μL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 9 mg of the title compound in 22% overall yield (95% purity) as a 1:7.4 mixture of diastereomers.

HR-MS (ESI) calculated for $C_{37}H_{52}N_{13}O_9$ [M+H]$^+$: 822.4005. found: 822.4006.

HPLC Method A:
Retention time (major diastereomer) 6.39 min
Retention time (minor diastereomer) 5.11 min (17)

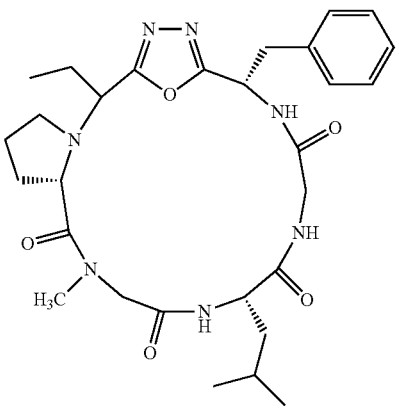

cyclo[PSarLGF]odz/ethyl

The peptide NH-Pro-Sar-Leu-Gly-Phe-CO$_2$H (25.2 mg, 0.05 mmol, 1 eq) was dissolved in a mixture of 1:1 Dichloroethane:Acetonitrile (2 mL). Propionaldehyde (5.4 μL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 8 mg of the title compound in 28% overall yield as a single diastereomer.

HR-MS (ESI) calculated for $C_{29}H_{42}N_7O_5$ [M+H]$^+$: 568.3242. found: 568.3252.

HPLC Method A:
Retention time 6.14 min

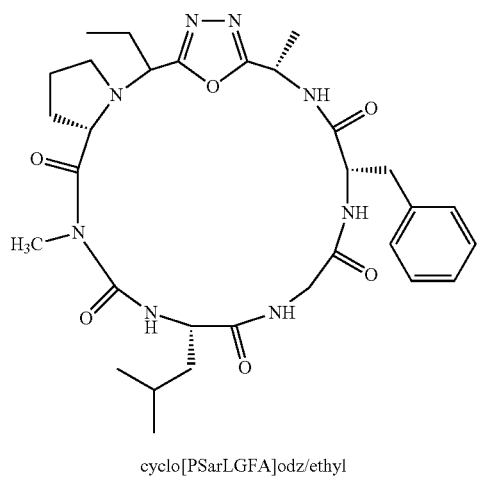

cyclo[PSarLGFA]odz/ethyl

The peptide NH-Pro-Sar-Leu-Gly-Phe-Ala-CO$_2$H (28.7 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 13.4 mg of the title compound in 42% overall yield as a single diastereomer.

HR-MS (ESI) calculated for $C_{32}H_{47}N_8O_6$ [M+H]$^+$: 639.3613. found: 639.3617.

HPLC Method A:
Retention time 6.13 min

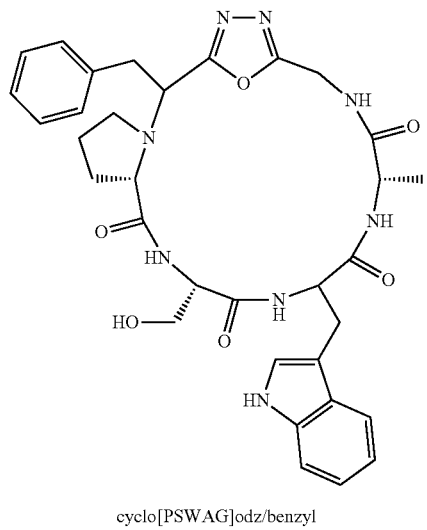

cyclo[PSWAG]odz/benzyl

The peptide NH-Pro-Ser(O$^t$Bu)-Trp(Boc)-Ala-Gly-CO$_2$H (33.6 mg, 0.05 mmol, 1 eq) was dissolved in a mixture of 1:1 Dichloroethane:Acetonitrile (2 mL). Phenylacetaldehyde (8.35 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 8.3 mg of the title compound in 26% overall yield as a 2.1:1 mixture of diastereomers.

HR-MS (ESI) calculated for $C_{33}H_{39}N_8O_6$ [M+H]$^+$: 643.2987. found: 643.298.

HPLC Method A:
Retention time (major diastereomer) 7.46 min
Retention time (minor diastereomer) 7.65 min

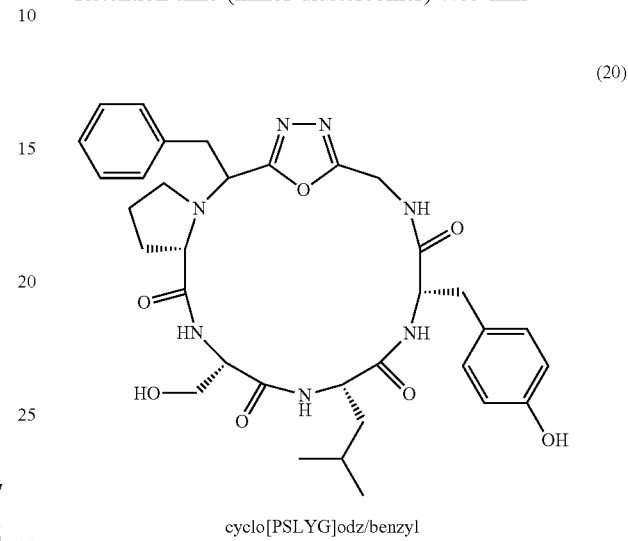

cyclo[PSLYG]odz/benzyl

The peptide NH-Pro-Ser(O$^t$Bu)-Leu-Tyr(O$^t$Bu)-Gly-CO$_2$H (32.4 mg, 0.05 mmol, 1 eq) was dissolved in a mixture of 1:1 Dichloroethane:Acetonitrile (2 mL). Phenylacetaldehyde (8.35 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 7 mg of the title compound in 22% overall yield as a single diastereomer.

HR-MS (ESI) calculated for $C_{34}H_{44}N_7O_7$ [M+H]$^+$: 662.3297. found: 662.3294.

HPLC Method A:
Retention time 7.38 min

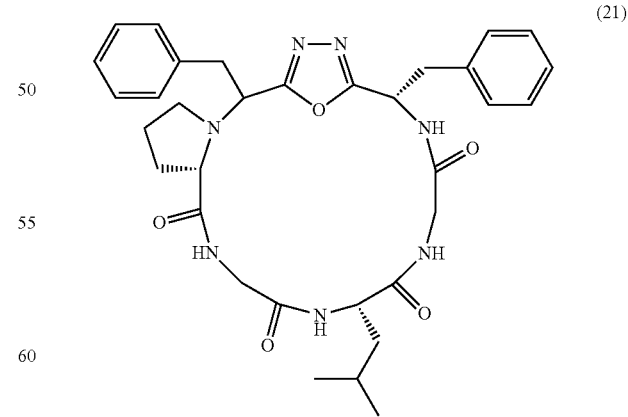

cyclo[PGLGF]odz/benzyl

The peptide NH-Pro-Gly-Leu-Gly-Phe-CO$_2$H (24.5 mg, 0.05 mmol, 1 eq) was dissolved in a mixture of 1:1 Dichloroethane:Acetonitrile (2 mL). Phenylacetaldehyde (8.35 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 9 mg of the title compound in 29% overall yield as a single diastereomer. The diastereoselectivity of the crude reaction was 2.7:1.

HR-MS (ESI) calculated for $C_{33}H_{42}N_7O_5$ [M+H]$^+$: 616.3242. found: 616.3244.

HPLC Method B:
Retention time (major diastereomer) 3.81 min

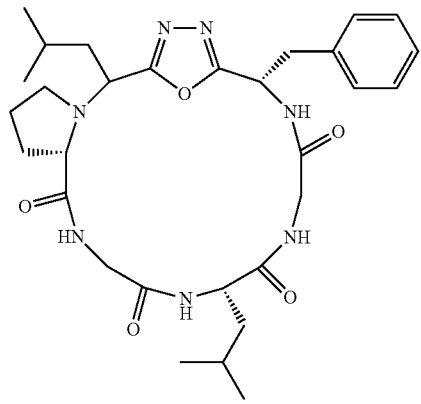

cyclo[PGLGF]odz/iBu

The peptide NH-Pro-Gly-Leu-Gly-Phe-CO$_2$H (24.5 mg, 0.05 mmol, 1 eq) was dissolved in a mixture of 1:1 Dichloroethane:Acetonitrile (2.5 mL). Isovaleraldehyde (8.8 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 8.9 mg of the title compound in 32% overall yield as a 6.3:1 mixture of diastereomers.

HR-MS (ESI) calculated for $C_{30}H_{43}N_7O_5$ [M+H]$^+$: 582.3326. found: 582.3399.

HPLC Method A:
Retention time (major diastereomer) 9.01 min
Retention time (minor diastereomer) 9.35 min

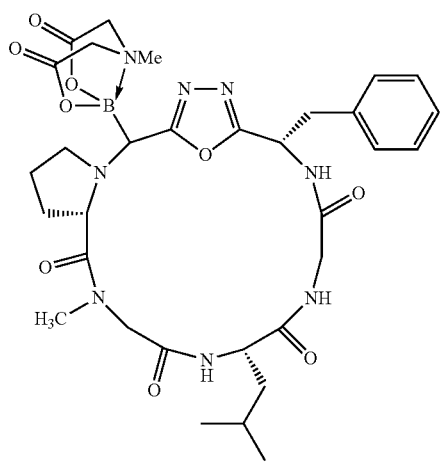

cyclo[PSarLGF]odz/α-borylaldehyde

The peptide NH-Pro-Sar-Leu-Gly-Phe-CO$_2$H was cyclized at 0.05 mmol scale with α-MIDA-borylaldehyde (1.5 eq) and (N-isocyanimino)triphenylphosphorane (1 eq). After cyclization, deprotection, and reverse phase purification the pure fractions were pooled and lyophilized to afford 10 mg of the title compound in 28% overall yield.

HR-MS (ESI) calculated for $C_{33}H_{46}BN_8O_9$ [M+H]$^+$: 708.348. found: 708.3484.

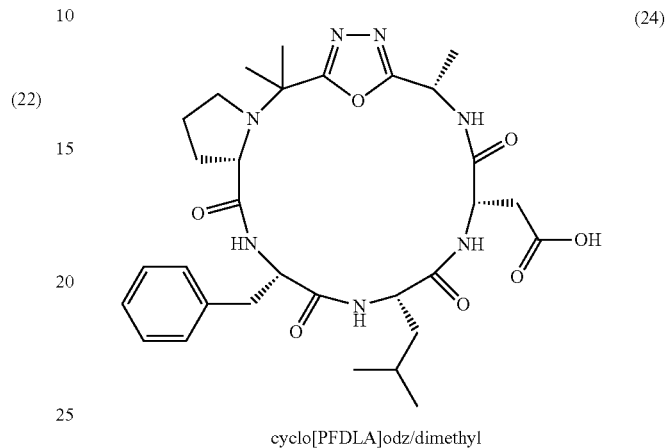

cyclo[PFDLA]odz/dimethyl

The peptide NH-Pro-Phe-Leu-Asp(O$^t$Bu)-Ala-CO$_2$H (30.9 mg, 0.05 mmol, 1 eq) was dissolved in a mixture of 1:1 Dichloroethane:Acetonitrile (2 mL). Acetone (30% by volume) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 3 mg of the title compound in 10% overall yield.

HR-MS (ESI) calculated for $C_{31}H_{43}N_7O_7$ [M+H]$^+$: 626.3224. found: 626.3230.

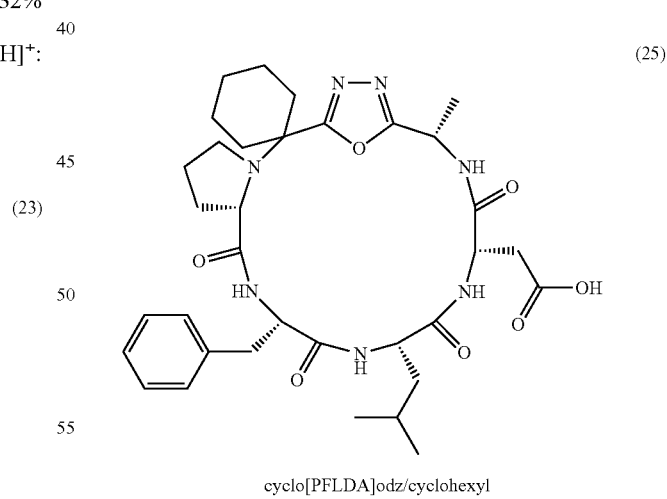

cyclo[PFLDA]odz/cyclohexyl

The peptide NH-Pro-Phe-Leu-Asp(O$^t$Bu)-Ala-CO$_2$H (30.9 mg, 0.05 mmol, 1 eq) was dissolved in a mixture of 1:1 Dichloroethane:Acetonitrile (2 mL). Cyclohexanone (0.1 mmol, 2 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 3.3 mg of the title compound in 10% overall yield.

HR-MS (ESI) calculated for $C_{34}H_{37}N_7O_7$ [M+H]$^+$: 666.3537. found: 666.3539

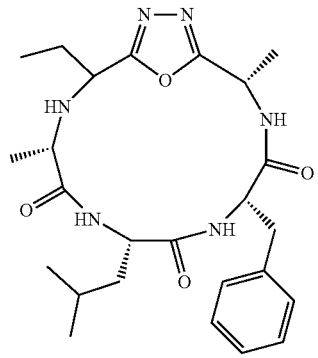

(26)

cyclo[ALFA]odz/ethyl

The peptide $NH_2$-Ala-Leu-Phe-Ala-$CO_2H$ (21.0 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 4.9 mg of the title compound in 20% overall yield as a 8.3:1 mixture of diastereomers.

HR-MS (ESI) calculated for $C_{25}H_{36}N_6O_4$ [M+H]$^+$: 485.2798. found: 485.2866.

HPLC Method A:
Retention time (major diastereomer) 8.61 min
Retention time (minor diastereomer) 9.05 min

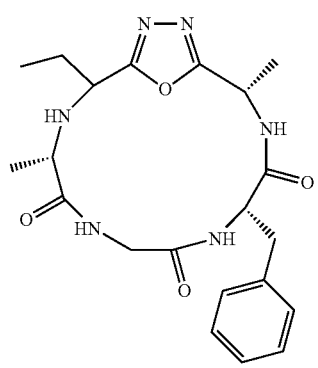

(27)

cyclo[AGFA]odz/ethyl

The peptide $NH_2$-Ala-Gly-Phe-Ala-$CO_2H$ (18.2 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 5.2 mg of the title compound in 24% overall yield as a 2.8:1 mixture of diastereomers.

HR-MS (ESI) calculated for $C_{21}H_{28}N_6O_4$ [M+H]$^+$: 429.2172. found: 429.2238.

HPLC Method A:
Retention time (major diastereomer) 4.83 min
Retention time (minor diastereomer) 5.01 min

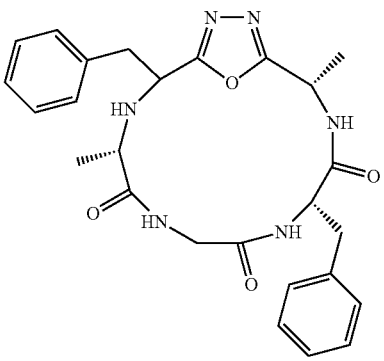

(28)

cyclo[AGFA]odz/benzyl

The peptide $NH_2$-Ala-Gly-Phe-Ala-$CO_2H$ (18.2 mg, 0.05 mmol, 1 eq) was dissolved in a mixture of 1:1 Dichloroethane:Acetonitrile (2 mL). Phenylacetaldehyde (8.35 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 8.0 mg of the title compound in 32% overall yield as a 1.3:1 mixture of diastereomers.

HR-MS (ESI) calculated for $C_{26}H_{30}N_6O_4$ [M+H]$^+$: 491.2329. found: 491.2397.

HPLC Method A:
Retention time (major diastereomer) 6.85 min
Retention time (minor diastereomer) 6.73 min

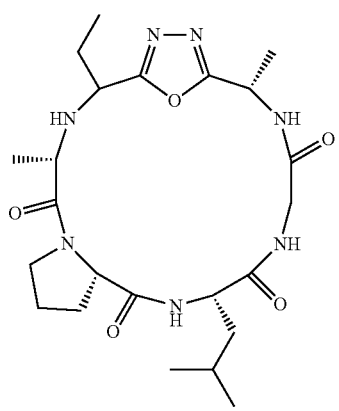

(29)

cyclo[APLGA]odz/ethyl

The peptide $NH_2$-Ala-Pro-Leu-Gly-Ala-$CO_2H$ (21.4 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 3.7 mg of the title compound in 15% overall yield as a 1:2.6 mixture of diastereomers.

HR-MS (ESI) calculated for $C_{23}H_{38}N_7O_5$ [M+H]$^+$: 492.2916. found: 492.2918.

HPLC Method A:

Retention time (major diastereomer) 4.98 min

Retention time (minor diastereomer) 4.76 min

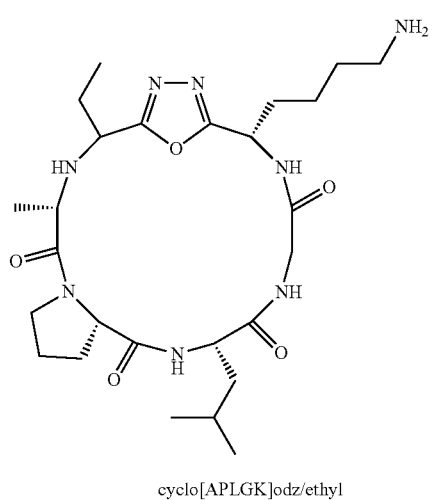

cyclo[APLGK]odz/ethyl (30)

The peptide NH$_2$-Ala-Pro-Leu-Gly-Lys(Boc)-CO$_2$H was cyclized at 0.05 mmol scale with propionaldehyde (1.5 eq) and (N-isocyanimino)triphenylphosphorane (1 eq). After cyclization, deprotection, and reverse phase purification the pure fractions were pooled and lyophilized to afford 16.3 mg of the title compound in 60% overall yield.

HR-MS (ESI) calculated for $C_{26}H_{45}N_8O_5$ [M+H]$^+$: 549.3507. found: 549.3507.

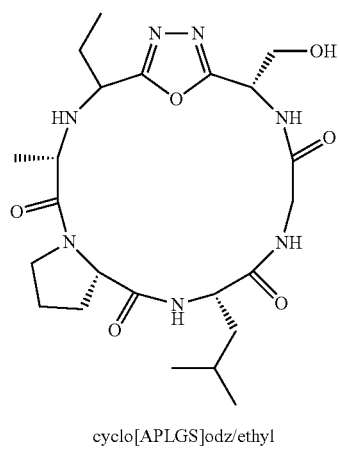

cyclo[APLGS]odz/ethyl (31)

The peptide NH$_2$-Ala-Pro-Leu-Gly-Ser(OtBu)—CO$_2$H was cyclized at 0.05 mmol scale with propionaldehyde (1.5 eq) and (N-isocyanimino)triphenylphosphorane (1 eq). After cyclization, deprotection, and reverse phase purification the pure fractions were pooled and lyophilized to afford 24 mg of the title compound in 70% overall yield.

HR-MS (ESI) calculated for $C_{23}H_{38}N_7O_6$ [M+H]$^+$: 508.2878. found: 508.2871.

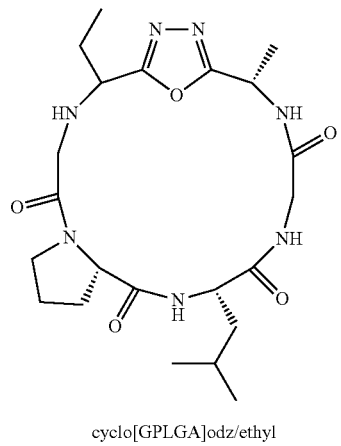

cyclo[GPLGA]odz/ethyl (32)

The peptide NH-Gly-Pro-Leu-Gly-Phe-CO$_2$H (20.7 mg, 0.05 mmol, 1 eq) was dissolved in a mixture of 1:1 Dichloroethane:Acetonitrile (2 mL). Propionaldehyde (5.4 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 4.8 mg of the title compound in 20% overall yield as a 1:1 mixture of diastereomers.

HR-MS (ESI) calculated for $C_{22}H_{36}N_7O_5$ [M+H]$^+$: 478.2772. found: 478.2774.

HPLC Method A:

Retention time (major diastereomer) 4.73 min

Retention time (minor diastereomer) 4.90 min

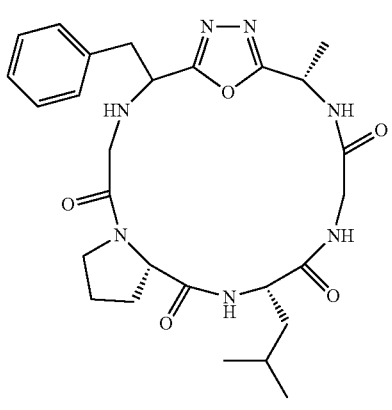

cyclo[GPLGA]odz/benzyl (33)

The peptide NH$_2$-Gly-Pro-Leu-Gly-Ala-CO$_2$H (20.7 mg, 0.05 mmol, 1 eq) was dissolved in a mixture of 1:1 Dichloroethane:Acetonitrile (2 mL). Phenylacetaldehyde (8.35 µL, 0.075 mmol, 1.5 eq) and (N-isocyanimino)triphenylphosphorane (15.1 mg, 0.05 mmol, 1 eq) were added to the reaction mixture. After cyclization, deprotection, and reverse phase purification the pure fractions were pooled and lyophilized to afford 3.5 mg of the title compound in 13% overall yield as a 1.1:1 mixture of diastereomers.

HR-MS (ESI) calculated for $C_{27}H_{38}N_7O_5$ [M+H]$^+$: 540.2929. found: 540.2923.

HPLC Method A:
Retention time (major diastereomer) 6.58 min
Retention time (minor diastereomer) 6.45 min

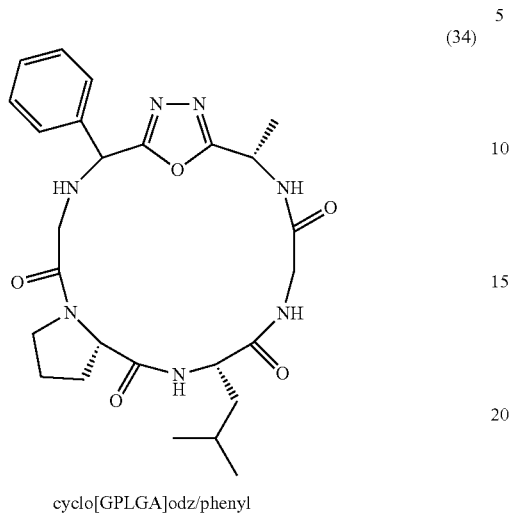

(34)

cyclo[GPLGA]odz/phenyl

The peptide $NH_2$-Gly-Pro-Leu-Gly-Ala-$CO_2H$ was cyclized at 0.05 mmol scale with benzaldehyde (1.5 eq) and (N-isocyanimino)triphenylphosphorane (1 eq). After cyclization, deprotection, and reverse phase purification the pure fractions were pooled and lyophilized to afford 6.7 mg of the title compound in 25% overall yield.

HR-MS (ESI) calculated for $C_{26}H_{36}N_7O_5$ $[M+H]^+$: 526.2772. found: 526.278.

TABLE 1

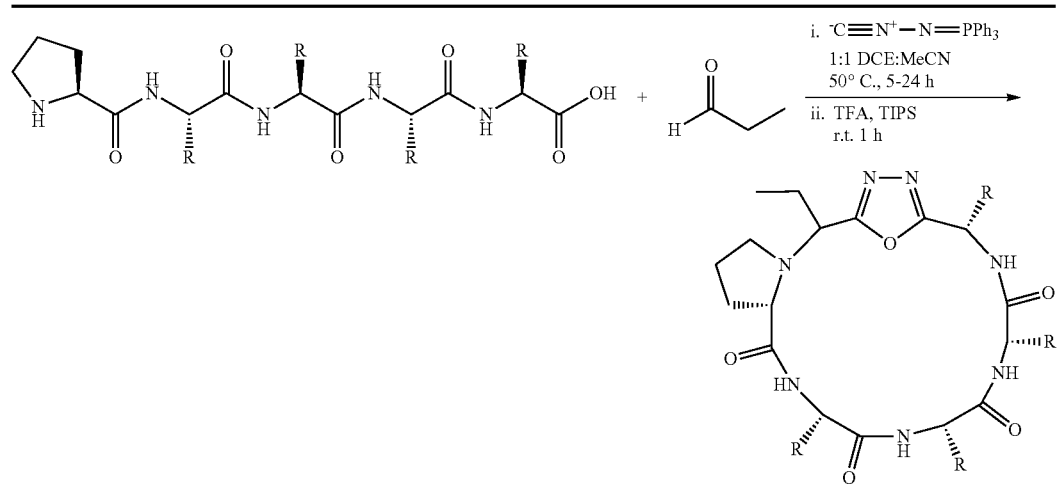

| Compound | Length | Sequence | Aldehyde | Isolated Yield |
|---|---|---|---|---|
| 1 | 5 mer | PGLGF | propionaldehyde | 68% |
| 2 | 5 mer | PDAWG | propionaldehyde | 22% |
| 3 | 5 mer | PRGDA | propionaldehyde | 70% |
| 4 | 5 mer | PWASG | propionaldehyde | 28% |
| 5 | 5 mer | PSLYA | propionaldehyde | 24% |
| 6 | 5 mer | PLDFA | propionaldehyde | 52% |
| 7 | 5 mer | PFDLA | propionaldehyde | 45% |
| 8 | 5 mer | PGLAF | propionaldehyde | 23% |
| 9 | 5 mer | PALGF | propionaldehyde | 25% |
| 10 | 5 mer | PALAF | propionaldehyde | 20% |
| 11 | 5 mer | PFLLF | propionaldehyde | 25% |
| Average | | | | 38% |

Oxadiazole containing cyclic peptides of varying sequence composition.

TABLE 2

| Compound | Length | Sequence | Aldehyde | Isolated Yield |
|---|---|---|---|---|
| 12 | 4 mer | PAFA | propionaldehyde | 23% |
| 13 | 6 mer | PASWKG | propionaldehyde | 7% |
| 14 | 6 mer | PGLGFA | propionaldehyde | 41% |
| 15 | 6 mer | PDAWYG | propionaldehyde | 28% |
| 16 | 7 mer | PGRGDWA | propionaldehyde | 22% |

Oxadiazole containing cyclic peptides of varying sequence length and composition.

TABLE 3

| Compound | Length | Sequence | Aldehyde | Isolated Yield |
|---|---|---|---|---|
| 17 | 5 mer | PSarLGF | propionaldehyde | 28% |
| 18 | 6 mer | PSarLGFA | propionaldehyde | 42% |

N-methylated oxadiazole containing cyclic peptides of varying sequence length and composition.

TABLE 4

| Compound | Length | Sequence | Aldehyde | Isolated Yield |
|---|---|---|---|---|
| 19 | 5 mer | PSWAG | phenylacetaldehyde | 26% |
| 20 | 5 mer | PSLYG | phenylacetaldehyde | 22% |
| 21 | 5 mer | PGLGF | phenylacetaldehyde | 29% |
| 22 | 5 mer | PGLGF | isovaleraldehyde | 32% |
| 23 | 5 mer | PSarLGF | α-borylaldehyde | 28% |

Oxadiazole Containing Cyclic Peptides with Varying Aldehyde Components

TABLE 5

| Compound | Length | Sequence | Ketone | Isolated Yield |
|---|---|---|---|---|
| 24 | 5 mer | PFLDA | Acetone | 10% |
| 25 | 5 mer | PFLDA | Cyclohexanone | 10% |

Oxadiazole Containing Cyclic Peptides with
Varying Ketone Components

TABLE 6

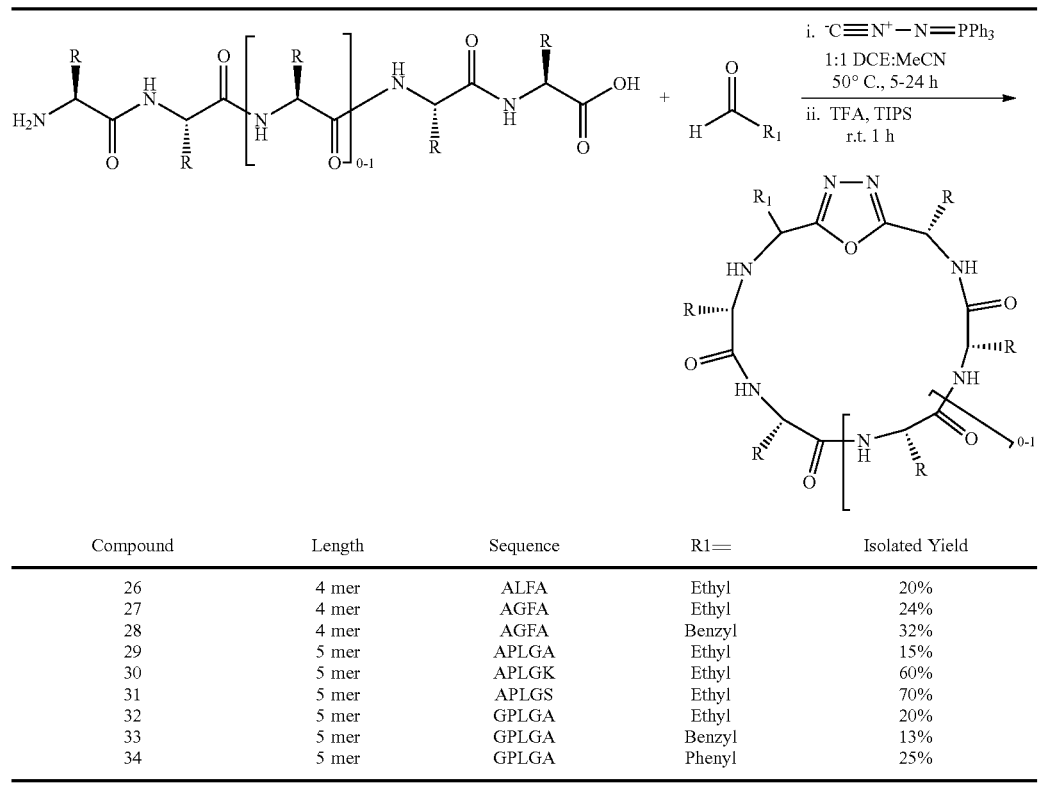

| Compound | Length | Sequence | R1= | Isolated Yield |
|---|---|---|---|---|
| 26 | 4 mer | ALFA | Ethyl | 20% |
| 27 | 4 mer | AGFA | Ethyl | 24% |
| 28 | 4 mer | AGFA | Benzyl | 32% |
| 29 | 5 mer | APLGA | Ethyl | 15% |
| 30 | 5 mer | APLGK | Ethyl | 60% |
| 31 | 5 mer | APLGS | Ethyl | 70% |
| 32 | 5 mer | GPLGA | Ethyl | 20% |
| 33 | 5 mer | GPLGA | Benzyl | 13% |
| 34 | 5 mer | GPLGA | Phenyl | 25% |

Oxadiazole Containing Cyclic Peptides with
Varying Aldehyde Components

TABLE 7

| | |
|---|---|
| Identification code | d15126 |
| Empirical formula | C28H42N7O6.50 |
| Formula weight | 580.68 |
| Temperature | 147(2) K |
| Wavelength | 1.54178 Å |
| Crystal system | Tetragonal |
| Space group | $P4_12_12$ |
| Unit cell dimensions | a = 10.4819(3) Å |
| | b = 10.4819(3) Å |
| | c = 57.620(2) Å |
| Volume | 6330.7(4) Å$^3$ |
| Z | 8 |
| Density (calculated) | 1.219 Mg/m$^3$ |
| Absorption coefficient | 0.724 mm$^{-1}$ |
| F(000) | 2488 |
| Crystal size | 0.350 × 0.200 × 0.010 mm$^3$ |
| Theta range for data collection | 3.068 to 67.215° |
| Index ranges | −7 <= h <= 12, −12 <= k <= 11, −68 <= l <= 68 |
| Reflections collected | 36843 |
| Independent reflections | 5613 [R(int) = 0.0399] |
| Completeness to theta = 67.215° | 99.3% |
| Absorption correction | Semi-empirical from equivalents |
| Max. and min. transmission | 0.7529 and 0.6702 |
| Refinement method | Full-matrix least-squares on F$^2$ |
| Data/restraints/parameters | 5613/23/438 |
| Goodness-of-fit on F$^2$ | 1.082 |
| Final R indices [I > 2sigma(I)] | R1 = 0.0386, wR2 = 0.0992 |
| R indices (all data) | R1 = 0.0399, wR2 = 0.1000 |
| Absolute structure parameter | 0.12(6) |
| Extinction coefficient | n/a |
| Largest diff. peak and hole | 0.352 and −0.198 e · Å$^{-3}$ |

Crystal Data and Structure Refinement for d15126

TABLE 8

| | x | y | z | U(eq) |
|---|---|---|---|---|
| O(1) | 5419(1) | 5844(2) | 4496(1) | 30(1) |
| O(2) | 9428(2) | 6898(2) | 4926(1) | 36(1) |
| O(3) | 10383(2) | 4176(2) | 4420(1) | 53(1) |
| O(4) | 7119(2) | 3813(2) | 4372(1) | 35(1) |
| O(5) | 4620(2) | 2869(2) | 3754(1) | 60(1) |
| N(1) | 3855(2) | 6504(2) | 4717(1) | 41(1) |
| N(2) | 5005(2) | 7072(2) | 4796(1) | 36(1) |
| N(3) | 8029(2) | 5831(2) | 4699(1) | 27(1) |
| N(4) | 9382(2) | 3565(2) | 4748(1) | 31(1) |
| N(5) | 8544(2) | 2531(2) | 4195(1) | 37(1) |
| N(6) | 5732(2) | 4199(2) | 3987(1) | 47(1) |
| C(2) | 4150(2) | 5804(2) | 4544(1) | 35(1) |
| C(3) | 5881(2) | 6649(2) | 4661(1) | 25(1) |
| C(4) | 7265(2) | 6957(2) | 4649(1) | 26(1) |
| C(5) | 9066(2) | 5899(2) | 4833(1) | 28(1) |
| C(6) | 9795(2) | 4670(2) | 4878(1) | 33(1) |
| C(7) | 9706(2) | 3414(3) | 4525(1) | 35(1) |
| C(9) | 7543(2) | 3312(2) | 4195(1) | 34(1) |
| C(10) | 6946(3) | 3570(3) | 3960(1) | 52(1) |
| C(11) | 4655(3) | 3768(3) | 3894(1) | 49(1) |
| C(13) | 3703(3) | 3561(3) | 4440(1) | 53(1) |
| C(14) | 3589(4) | 3212(3) | 4692(1) | 69(1) |
| C(15) | 7601(2) | 7505(2) | 4410(1) | 34(1) |
| C(16) | 6736(2) | 8586(2) | 4342(1) | 35(1) |
| C(17) | 5902(3) | 8472(3) | 4156(1) | 41(1) |
| C(18) | 5106(3) | 9468(3) | 4095(1) | 50(1) |
| C(19) | 5132(3) | 10587(3) | 4219(1) | 54(1) |
| C(20) | 5931(3) | 10709(3) | 4408(1) | 51(1) |
| C(21) | 6731(3) | 9715(3) | 4469(1) | 43(1) |
| C(8) | 9204(3) | 2211(3) | 4410(1) | 39(1) |
| C(22) | 10203(5) | 1167(5) | 4354(1) | 49(1) |
| C(23) | 10969(4) | 687(5) | 4562(1) | 60(2) |
| C(24) | 10172(5) | 41(6) | 4740(1) | 77(2) |

TABLE 8-continued

|  | x | y | z | U(eq) |
|---|---|---|---|---|
| C(25) | 12024(6) | −177(7) | 4477(1) | 95(2) |
| C(8A) | 9204(3) | 2211(3) | 4410(1) | 39(1) |
| C(22A) | 10510(7) | 1589(7) | 4351(2) | 44(3) |
| C(23A) | 10358(8) | 137(7) | 4336(1) | 50(2) |
| C(24A) | 11288(12) | −470(11) | 4175(2) | 87(4) |
| C(25A) | 10406(12) | −432(11) | 4574(2) | 77(3) |
| C(1) | 3360(2) | 4956(3) | 4391(1) | 49(1) |
| N(7) | 3604(3) | 5363(3) | 4151(1) | 51(1) |
| C(12) | 3444(4) | 4460(5) | 3956(1) | 68(2) |
| C(26) | 3022(6) | 5301(4) | 3746(1) | 78(2) |
| C(27) | 3250(5) | 6663(4) | 3828(1) | 73(2) |
| C(28) | 2960(5) | 6560(4) | 4089(1) | 66(2) |
| C(1A) | 3360(2) | 4956(3) | 4391(1) | 49(1) |
| N(7A) | 3757(16) | 5357(18) | 4157(1) | 44(5) |
| C(12A) | 3518(17) | 4458(19) | 3964(2) | 44(5) |
| C(26A) | 2310(18) | 5009(16) | 3844(4) | 44(5) |
| C(27A) | 2480(20) | 6436(15) | 3875(3) | 44(5) |
| C(28A) | 3250(30) | 6615(13) | 4096(3) | 44(5) |
| O(1W) | 11990(2) | 7442(2) | 5050(1) | 46(1) |
| O(2W) | 10154(5) | 4741(4) | 3946(1) | 62(1) |

Atomic coordinates (×10⁴) and equivalent isotropic displacement parameters (Å²×10³) for d15126. U(eq) is defined as one third of the trace of the orthogonalized $U^{ij}$ tensor.

TABLE 9

| O(1)—C(2) | 1.359(3) |
|---|---|
| O(1)—C(3) | 1.364(3) |
| O(2)—C(5) | 1.233(3) |
| O(3)—C(7) | 1.227(3) |
| O(4)—C(9) | 1.231(3) |
| O(5)—C(11) | 1.238(3) |
| N(1)—C(2) | 1.280(3) |
| N(1)—N(2) | 1.418(3) |
| N(2)—C(3) | 1.279(3) |
| N(3)—C(5) | 1.337(3) |
| N(3)—C(4) | 1.455(3) |
| N(3)—H(3N) | 0.89(3) |
| N(4)—C(7) | 1.335(3) |
| N(4)—C(6) | 1.449(3) |
| N(4)—H(4N) | 0.87(3) |
| N(5)—C(9) | 1.331(3) |
| N(5)—C(8A) | 1.456(3) |
| N(5)—C(8) | 1.456(3) |
| N(5)—H(5N) | 0.88(3) |
| N(6)—C(11) | 1.330(4) |
| N(6)—C(10) | 1.442(4) |
| N(6)—H(6N) | 0.88(4) |
| C(2)—C(1A) | 1.499(4) |
| C(2)—C(1) | 1.499(4) |
| C(3)—C(4) | 1.487(3) |
| C(4)—C(15) | 1.537(3) |
| C(4)—H(4A) | 1.0000 |
| C(5)—C(6) | 1.520(3) |
| C(6)—H(6A) | 0.9900 |
| C(6)—H(6B) | 0.9900 |
| C(7)—C(8A) | 1.519(4) |
| C(7)—C(8) | 1.519(4) |
| C(9)—C(10) | 1.516(4) |
| C(10)—H(10A) | 0.9900 |
| C(10)—H(10B) | 0.9900 |
| C(11)—C(12A) | 1.452(11) |
| C(11)—C(12) | 1.507(5) |
| C(13)—C(14) | 1.504(5) |
| C(13)—C(1A) | 1.531(4) |
| C(13)—C(1) | 1.531(4) |
| C(13)—H(13A) | 0.9900 |
| C(13)—H(13B) | 0.9900 |
| C(14)—H(14A) | 0.9800 |
| C(14)—H(14B) | 0.9800 |
| C(14)—H(14C) | 0.9800 |
| C(15)—C(16) | 1.503(4) |
| C(15)—H(15A) | 0.9900 |
| C(15)—H(15B) | 0.9900 |
| C(16)—C(17) | 1.385(4) |
| C(16)—C(21) | 1.391(4) |
| C(17)—C(18) | 1.382(4) |
| C(17)—H(17A) | 0.9500 |
| C(18)—C(19) | 1.374(4) |
| C(18)—H(18A) | 0.9500 |
| C(19)—C(20) | 1.380(5) |
| C(19)—H(19A) | 0.9500 |
| C(20)—C(21) | 1.383(4) |
| C(20)—H(20A) | 0.9500 |
| C(21)—H(21A) | 0.9500 |
| C(8)—C(22) | 1.548(4) |
| C(8)—H(8) | 1.0000 |
| C(22)—C(23) | 1.531(7) |
| C(22)—H(22A) | 0.9900 |
| C(22)—H(22B) | 0.9900 |
| C(23)—C(24) | 1.487(7) |
| C(23)—C(25) | 1.512(6) |
| C(23)—H(23) | 1.0000 |
| C(24)—H(24A) | 0.9800 |
| C(24)—H(24B) | 0.9800 |
| C(24)—H(24C) | 0.9800 |
| C(25)—H(25A) | 0.9800 |
| C(25)—H(25B) | 0.9800 |
| C(25)—H(25C) | 0.9800 |
| C(8A)—C(22A) | 1.552(6) |
| C(8A)—H(8A) | 1.0000 |
| C(22A)—C(23A) | 1.534(8) |
| C(22A)—H(22C) | 0.9900 |
| C(22A)—H(22D) | 0.9900 |
| C(23A)—C(24A) | 1.488(9) |
| C(23A)—C(25A) | 1.500(8) |
| C(23A)—H(23A) | 1.0000 |
| C(24A)—H(24D) | 0.9800 |
| C(24A)—H(24E) | 0.9800 |
| C(24A)—H(24F) | 0.9800 |
| C(25A)—H(25D) | 0.9800 |
| C(25A)—H(25E) | 0.9800 |
| C(25A)—H(25F) | 0.9800 |
| C(1)—N(7) | 1.470(4) |
| C(1)—H(1A) | 1.0000 |
| N(7)—C(28) | 1.469(4) |
| N(7)—C(12) | 1.478(4) |
| C(12)—C(26) | 1.563(6) |
| C(12)—H(12A) | 1.0000 |
| C(26)—C(27) | 1.523(6) |
| C(26)—H(26A) | 0.9900 |
| C(26)—H(26B) | 0.9900 |
| C(27)—C(28) | 1.540(7) |
| C(27)—H(27A) | 0.9900 |
| C(27)—H(27B) | 0.9900 |
| C(28)—H(28A) | 0.9900 |
| C(28)—H(28B) | 0.9900 |
| C(1A)—N(7A) | 1.474(7) |
| C(1A)—H(1AA) | 1.0000 |
| N(7A)—C(28A) | 1.462(7) |
| N(7A)—C(12A) | 1.480(7) |
| C(12A)—C(26A) | 1.555(8) |
| C(12A)—H(12B) | 1.0000 |
| C(26A)—C(27A) | 1.517(8) |
| C(26A)—H(26C) | 0.9900 |
| C(26A)—H(26D) | 0.9900 |
| C(27A)—C(28A) | 1.521(9) |
| C(27A)—H(27C) | 0.9900 |
| C(27A)—H(27D) | 0.9900 |
| C(28A)—H(28C) | 0.9900 |
| C(28A)—H(28D) | 0.9900 |
| O(1W)—H(1WA) | 0.85(4) |
| O(1W)—H(1WB) | 0.85(4) |
| O(2W)—H(2WA) | 0.8401 |
| O(2W)—H(2WB) | 0.8400 |
| C(2)—O(1)—C(3) | 102.95(17) |
| C(2)—N(1)—N(2) | 106.44(19) |
| C(3)—N(2)—N(1) | 105.86(18) |
| C(5)—N(3)—C(4) | 121.2(2) |
| C(5)—N(3)—H(3N) | 122.2(17) |
| C(4)—N(3)—H(3N) | 116.4(18) |
| C(7)—N(4)—C(6) | 121.3(2) |
| C(7)—N(4)—H(4N) | 120(2) |
| C(6)—N(4)—H(4N) | 118(2) |

TABLE 9-continued

| | |
|---|---|
| C(9)—N(5)—C(8A) | 121.0(2) |
| C(9)—N(5)—C(8) | 121.0(2) |
| C(9)—N(5)—H(5N) | 121(2) |
| C(8A)—N(5)—H(5N) | 118(2) |
| C(8)—N(5)—H(5N) | 118(2) |
| C(11)—N(6)—C(10) | 123.4(2) |
| C(11)—N(6)—H(6N) | 110(2) |
| C(10)—N(6)—H(6N) | 125(2) |
| N(1)—C(2)—O(1) | 112.2(2) |
| N(1)—C(2)—C(1A) | 131.7(2) |
| O(1)—C(2)—C(1A) | 116.1(2) |
| N(1)—C(2)—C(1) | 131.7(2) |
| O(1)—C(2)—C(1) | 116.1(2) |
| N(2)—C(3)—O(1) | 112.5(2) |
| N(2)—C(3)—C(4) | 130.8(2) |
| O(1)—C(3)—C(4) | 116.59(18) |
| N(3)—C(4)—C(3) | 110.61(19) |
| N(3)—C(4)—C(15) | 110.68(18) |
| C(3)—C(4)—C(15) | 110.29(19) |
| N(3)—C(4)—H(4A) | 108.4 |
| C(3)—C(4)—H(4A) | 108.4 |
| C(15)—C(4)—H(4A) | 108.4 |
| O(2)—C(5)—N(3) | 123.0(2) |
| O(2)—C(5)—C(6) | 119.4(2) |
| N(3)—C(5)—C(6) | 117.5(2) |
| N(4)—C(6)—C(5) | 116.01(19) |
| N(4)—C(6)—H(6A) | 108.3 |
| C(5)—C(6)—H(6A) | 108.3 |
| N(4)—C(6)—H(6B) | 108.3 |
| C(5)—C(6)—H(6B) | 108.3 |
| H(6A)—C(6)—H(6B) | 107.4 |
| O(3)—C(7)—N(4) | 122.8(2) |
| O(3)—C(7)—C(8A) | 121.6(2) |
| N(4)—C(7)—C(8A) | 115.5(2) |
| O(3)—C(7)—C(8) | 121.6(2) |
| N(4)—C(7)—C(8) | 115.5(2) |
| O(4)—C(9)—N(5) | 123.2(2) |
| O(4)—C(9)—C(10) | 121.0(2) |
| N(5)—C(9)—C(10) | 115.7(2) |
| N(6)—C(10)—C(9) | 110.5(2) |
| N(6)—C(10)—H(10A) | 109.6 |
| C(9)—C(10)—H(10A) | 109.6 |
| N(6)—C(10)—H(10B) | 109.6 |
| C(9)—C(10)—H(10B) | 109.6 |
| H(10A)—C(10)—H(10B) | 108.1 |
| O(5)—C(11)—N(6) | 123.1(3) |
| O(5)—C(11)—C(12A) | 122.4(9) |
| N(6)—C(11)—C(12A) | 114.5(9) |
| O(5)—C(11)—C(12) | 119.8(3) |
| N(6)—C(11)—C(12) | 117.0(3) |
| C(14)—C(13)—C(1A) | 113.0(3) |
| C(14)—C(13)—C(1) | 113.0(3) |
| C(14)—C(13)—H(13A) | 109.0 |
| C(1)—C(13)—H(13A) | 109.0 |
| C(14)—C(13)—H(13B) | 109.0 |
| C(1)—C(13)—H(13B) | 109.0 |
| H(13A)—C(13)—H(13B) | 107.8 |
| C(13)—C(14)—H(14A) | 109.5 |
| C(13)—C(14)—H(14B) | 109.5 |
| H(14A)—C(14)—H(14B) | 109.5 |
| C(13)—C(14)—H(14C) | 109.5 |
| H(14A)—C(14)—H(14C) | 109.5 |
| H(14B)—C(14)—H(14C) | 109.5 |
| C(16)—C(15)—C(4) | 112.22(19) |
| C(16)—C(15)—H(15A) | 109.2 |
| C(4)—C(15)—H(15A) | 109.2 |
| C(16)—C(15)—H(15B) | 109.2 |
| C(4)—C(15)—H(15B) | 109.2 |
| H(15A)—C(15)—H(15B) | 107.9 |
| C(17)—C(16)—C(21) | 118.4(3) |
| C(17)—C(16)—C(15) | 121.1(2) |
| C(21)—C(16)—C(15) | 120.4(2) |
| C(18)—C(17)—C(16) | 120.9(3) |
| C(18)—C(17)—H(17A) | 119.6 |
| C(16)—C(17)—H(17A) | 119.6 |
| C(19)—C(18)—C(17) | 119.9(3) |
| C(19)—C(18)—H(18A) | 120.0 |
| C(17)—C(18)—H(18A) | 120.0 |
| C(18)—C(19)—C(20) | 120.1(3) |
| C(18)—C(19)—H(19A) | 119.9 |
| C(20)—C(19)—H(19A) | 119.9 |
| C(19)—C(20)—C(21) | 119.9(3) |
| C(19)—C(20)—H(20A) | 120.1 |
| C(21)—C(20)—H(20A) | 120.1 |
| C(20)—C(21)—C(16) | 120.7(3) |
| C(20)—C(21)—H(21A) | 119.7 |
| C(16)—C(21)—H(21A) | 119.7 |
| N(5)—C(8)—C(7) | 110.2(2) |
| N(5)—C(8)—C(22) | 107.9(3) |
| C(7)—C(8)—C(22) | 116.3(3) |
| N(5)—C(8)—H(8) | 107.3 |
| C(7)—C(8)—H(8) | 107.3 |
| C(22)—C(8)—H(8) | 107.3 |
| C(23)—C(22)—C(8) | 115.0(4) |
| C(23)—C(22)—H(22A) | 108.5 |
| C(8)—C(22)—H(22A) | 108.5 |
| C(23)—C(22)—H(22B) | 108.5 |
| C(8)—C(22)—H(22B) | 108.5 |
| H(22A)—C(22)—H(22B) | 107.5 |
| C(24)—C(23)—C(25) | 111.3(5) |
| C(24)—C(23)—C(22) | 113.4(4) |
| C(25)—C(23)—C(22) | 108.9(5) |
| C(24)—C(23)—H(23) | 107.7 |
| C(25)—C(23)—H(23) | 107.7 |
| C(22)—C(23)—H(23) | 107.7 |
| C(23)—C(24)—H(24A) | 109.5 |
| C(23)—C(24)—H(24B) | 109.5 |
| H(24A)—C(24)—H(24B) | 109.5 |
| C(23)—C(24)—H(24C) | 109.5 |
| H(24A)—C(24)—H(24C) | 109.5 |
| H(24B)—C(24)—H(24C) | 109.5 |
| C(23)—C(25)—H(25A) | 109.5 |
| C(23)—C(25)—H(25B) | 109.5 |
| H(25A)—C(25)—H(25B) | 109.5 |
| C(23)—C(25)—H(25C) | 109.5 |
| H(25A)—C(25)—H(25C) | 109.5 |
| H(25B)—C(25)—H(25C) | 109.5 |
| N(5)—C(8A)—C(7) | 110.2(2) |
| N(5)—C(8A)—C(22A) | 109.4(4) |
| C(7)—C(8A)—C(22A) | 98.0(4) |
| N(5)—C(8A)—H(8A) | 112.8 |
| C(7)—C(8A)—H(8A) | 112.8 |
| C(22A)—C(8A)—H(8A) | 112.8 |
| C(23A)—C(22A)—C(8A) | 109.7(6) |
| C(23A)—C(22A)—H(22C) | 109.7 |
| C(8A)—C(22A)—H(22C) | 109.7 |
| C(23A)—C(22A)—H(22D) | 109.7 |
| C(8A)—C(22A)—H(22D) | 109.7 |
| H(22C)—C(22A)—H(22D) | 108.2 |
| C(24A)—C(23A)—C(25A) | 112.3(7) |
| C(24A)—C(23A)—C(22A) | 113.1(7) |
| C(25A)—C(23A)—C(22A) | 109.7(7) |
| C(24A)—C(23A)—H(23A) | 107.1 |
| C(25A)—C(23A)—H(23A) | 107.1 |
| C(22A)—C(23A)—H(23A) | 107.1 |
| C(23A)—C(24A)—H(24D) | 109.5 |
| C(23A)—C(24A)—H(24E) | 109.5 |
| H(24D)—C(24A)—H(24E) | 109.5 |
| C(23A)—C(24A)—H(24F) | 109.5 |
| H(24D)—C(24A)—H(24F) | 109.5 |
| H(24E)—C(24A)—H(24F) | 109.5 |
| C(23A)—C(25A)—H(25D) | 109.5 |
| C(23A)—C(25A)—H(25E) | 109.5 |
| H(25D)—C(25A)—H(25E) | 109.5 |
| C(23A)—C(25A)—H(25F) | 109.5 |
| H(25D)—C(25A)—H(25F) | 109.5 |
| H(25E)—C(25A)—H(25F) | 109.5 |
| N(7)—C(1)—C(2) | 106.4(2) |
| N(7)—C(1)—C(13) | 114.1(3) |
| C(2)—C(1)—C(13) | 109.2(2) |
| N(7)—C(1)—H(1A) | 109.0 |
| C(2)—C(1)—H(1A) | 109.0 |
| C(13)—C(1)—H(1A) | 109.0 |
| C(28)—N(7)—C(1) | 113.5(3) |
| C(28)—N(7)—C(12) | 108.0(2) |
| C(1)—N(7)—C(12) | 120.6(3) |
| N(7)—C(12)—C(11) | 113.3(3) |
| N(7)—C(12)—C(26) | 105.1(3) |
| C(11)—C(12)—C(26) | 108.9(4) |
| N(7)—C(12)—H(12A) | 109.8 |

TABLE 9-continued

| | |
|---|---|
| C(11)—C(12)—H(12A) | 109.8 |
| C(26)—C(12)—H(12A) | 109.8 |
| C(27)—C(26)—C(12) | 104.1(3) |
| C(27)—C(26)—H(26A) | 110.9 |
| C(12)—C(26)—H(26A) | 110.9 |
| C(27)—C(26)—H(26B) | 110.9 |
| C(12)—C(26)—H(26B) | 110.9 |
| H(26A)—C(26)—H(26B) | 108.9 |
| C(26)—C(27)—C(28) | 101.8(4) |
| C(26)—C(27)—H(27A) | 111.4 |
| C(28)—C(27)—H(27A) | 111.4 |
| C(26)—C(27)—H(27B) | 111.4 |
| C(28)—C(27)—H(27B) | 111.4 |
| H(27A)—C(27)—H(27B) | 109.3 |
| N(7)—C(28)—C(27) | 102.0(3) |
| N(7)—C(28)—H(28A) | 111.4 |
| C(27)—C(28)—H(28A) | 111.4 |
| N(7)—C(28)—H(28B) | 111.4 |
| C(27)—C(28)—H(28B) | 111.4 |
| H(28A)—C(28)—H(28B) | 109.2 |
| N(7A)—C(1A)—C(2) | 102.2(7) |
| N(7A)—C(1A)—C(13) | 111.9(8) |
| C(2)—C(1A)—C(13) | 109.2(2) |
| N(7A)—C(1A)—H(1AA) | 111.1 |
| C(2)—C(1A)—H(1AA) | 111.1 |
| C(13)—C(1A)—H(1AA) | 111.1 |
| C(28A)—N(7A)—C(1A) | 112.1(9) |
| C(28A)—N(7A)—C(12A) | 109.4(6) |
| C(1A)—N(7A)—C(12A) | 117.3(9) |
| C(11)—C(12A)—N(7A) | 112.8(14) |
| C(11)—C(12A)—C(26A) | 136.9(12) |
| N(7A)—C(12A)—C(26A) | 103.6(7) |
| C(11)—C(12A)—H(12B) | 98.3 |
| N(7A)—C(12A)—H(12B) | 98.3 |
| C(26A)—C(12A)—H(12B) | 98.3 |
| C(27A)—C(26A)—C(12A) | 102.5(7) |
| C(27A)—C(26A)—H(26C) | 111.3 |
| C(12A)—C(26A)—H(26C) | 111.3 |
| C(27A)—C(26A)—H(26D) | 111.3 |
| C(12A)—C(26A)—H(26D) | 111.3 |
| H(26C)—C(26A)—H(26D) | 109.2 |
| C(26A)—C(27A)—C(28A) | 106.5(7) |
| C(26A)—C(27A)—H(27C) | 110.4 |
| C(28A)—C(27A)—H(27C) | 110.4 |
| C(26A)—C(27A)—H(27D) | 110.4 |
| C(28A)—C(27A)—H(27D) | 110.4 |
| H(27C)—C(27A)—H(27D) | 108.6 |
| N(7A)—C(28A)—C(27A) | 106.3(6) |
| N(7A)—C(28A)—H(28C) | 110.5 |
| C(27A)—C(28A)—H(28C) | 110.5 |
| N(7A)—C(28A)—H(28D) | 110.5 |
| C(27A)—C(28A)—H(28D) | 110.5 |
| H(28C)—C(28A)—H(28D) | 108.7 |
| H(1WA)—O(1W)—H(1WB) | 106(4) |
| H(2WA)—O(2W)—H(2WB) | 101.8 |

Symmetry transformations used to generate equivalent atoms:
Bond lengths [Å] and angles [°] for d15126.

TABLE 10

| | $U^{11}$ | $U^{22}$ | $U^{33}$ | $U^{23}$ | $U^{13}$ | $U^{12}$ |
|---|---|---|---|---|---|---|
| O(1) | 22(1) | 31(1) | 38(1) | −11(1) | 0(1) | −1(1) |
| O(2) | 24(1) | 41(1) | 42(1) | −10(1) | −2(1) | −5(1) |
| O(3) | 41(1) | 77(2) | 41(1) | −7(1) | 7(1) | −26(1) |
| O(4) | 34(1) | 40(1) | 32(1) | −12(1) | −2(1) | 7(1) |
| O(5) | 78(2) | 51(1) | 50(1) | −23(1) | −32(1) | 15(1) |
| N(1) | 22(1) | 48(1) | 53(1) | −15(1) | 5(1) | −4(1) |
| N(2) | 25(1) | 47(1) | 37(1) | −13(1) | 4(1) | −4(1) |
| N(3) | 24(1) | 27(1) | 29(1) | −4(1) | −1(1) | −2(1) |
| N(4) | 28(1) | 31(1) | 35(1) | −1(1) | 3(1) | 2(1) |
| N(5) | 34(1) | 39(1) | 38(1) | −17(1) | 5(1) | 2(1) |
| N(6) | 52(1) | 51(1) | 39(1) | −17(1) | −15(1) | 9(1) |
| C(2) | 21(1) | 34(1) | 49(1) | −9(1) | 1(1) | −2(1) |
| C(3) | 25(1) | 26(1) | 25(1) | −4(1) | 0(1) | −1(1) |
| C(4) | 23(1) | 27(1) | 30(1) | −6(1) | 1(1) | −2(1) |

TABLE 10-continued

| | $U^{11}$ | $U^{22}$ | $U^{33}$ | $U^{23}$ | $U^{13}$ | $U^{12}$ |
|---|---|---|---|---|---|---|
| C(5) | 21(1) | 36(1) | 26(1) | −3(1) | 4(1) | −4(1) |
| C(6) | 25(1) | 41(1) | 33(1) | −1(1) | −3(1) | 1(1) |
| C(7) | 22(1) | 43(1) | 39(1) | −2(1) | 1(1) | 2(1) |
| C(9) | 34(1) | 32(1) | 35(1) | −11(1) | 0(1) | −2(1) |
| C(10) | 51(2) | 70(2) | 34(1) | −16(1) | −5(1) | 12(2) |
| C(11) | 63(2) | 43(1) | 40(1) | −11(1) | −26(1) | 12(1) |
| C(13) | 34(2) | 40(2) | 83(2) | −19(2) | 2(1) | −7(1) |
| C(14) | 63(2) | 51(2) | 92(3) | −6(2) | 16(2) | −4(2) |
| C(15) | 31(1) | 33(1) | 37(1) | 0(1) | 9(1) | −2(1) |
| C(16) | 33(1) | 32(1) | 40(1) | 7(1) | 11(1) | −3(1) |
| C(17) | 46(2) | 40(1) | 35(1) | 6(1) | 6(1) | 1(1) |
| C(18) | 52(2) | 51(2) | 46(2) | 14(1) | −1(1) | 5(1) |
| C(19) | 49(2) | 38(2) | 75(2) | 15(2) | 2(2) | 6(1) |
| C(20) | 46(2) | 31(1) | 77(2) | 1(1) | 4(2) | 0(1) |
| C(21) | 38(1) | 35(1) | 55(2) | 1(1) | 4(1) | −4(1) |
| C(8) | 35(1) | 38(1) | 44(1) | −7(1) | 4(1) | 8(1) |
| C(22) | 38(2) | 31(3) | 77(3) | −14(2) | 11(2) | 10(2) |
| C(23) | 40(2) | 42(3) | 99(4) | 1(3) | 4(3) | 12(2) |
| C(24) | 52(3) | 62(3) | 118(5) | 17(3) | −1(3) | 16(3) |
| C(25) | 61(4) | 80(4) | 145(6) | 2(4) | 11(4) | 36(3) |
| C(8A) | 35(1) | 38(1) | 44(1) | −7(1) | 4(1) | 8(1) |
| C(1) | 22(1) | 42(2) | 82(2) | −25(2) | −7(1) | −2(1) |
| N(7) | 42(2) | 44(2) | 66(2) | −26(1) | −28(1) | 14(1) |
| C(12) | 60(2) | 59(2) | 84(3) | −41(2) | −50(2) | 19(2) |
| C(26) | 91(4) | 74(3) | 70(3) | −29(2) | −52(3) | 41(3) |
| C(27) | 88(4) | 66(3) | 64(2) | −18(2) | −47(2) | 29(2) |
| C(28) | 53(2) | 48(2) | 96(3) | −32(2) | −40(2) | 21(2) |
| C(1A) | 22(1) | 42(2) | 82(2) | −25(2) | −7(1) | −2(1) |
| O(1W) | 24(1) | 62(1) | 53(1) | −25(1) | 1(1) | −4(1) |
| O(2W) | 107(4) | 53(2) | 26(2) | 1(2) | 8(2) | −38(3) |

Anisotropic displacement parameters (Å$^2 \times 10^3$) for d15126. The anisotropic displacement factor exponent takes the form: $-2\pi^2[h^2 a^{*2}U^{11}+ \ldots +2\ h\ k\ a^*b^*U^{12}]$

TABLE 11

| | x | y | z | U(eq) |
|---|---|---|---|---|
| H(4A) | 7458 | 7618 | 4769 | 32 |
| H(6A) | 10707 | 4823 | 4844 | 40 |
| H(6B) | 9728 | 4466 | 5046 | 40 |
| H(10A) | 7524 | 4114 | 3867 | 62 |
| H(10B) | 6826 | 2754 | 3876 | 62 |
| H(13A) | 3135 | 3002 | 4348 | 63 |
| H(13B) | 4590 | 3403 | 4388 | 63 |
| H(14A) | 3705 | 2290 | 4710 | 103 |
| H(14B) | 2742 | 3454 | 4749 | 103 |
| H(14C) | 4244 | 3664 | 4781 | 103 |
| H(15A) | 8494 | 7812 | 4412 | 41 |
| H(15B) | 7537 | 6819 | 4292 | 41 |
| H(17A) | 5876 | 7699 | 4070 | 49 |
| H(18A) | 4542 | 9379 | 3967 | 60 |
| H(19A) | 4598 | 11278 | 4175 | 65 |
| H(20A) | 5931 | 11474 | 4496 | 62 |
| H(21A) | 7284 | 9803 | 4598 | 51 |
| H(8) | 8562 | 1824 | 4517 | 47 |
| H(22A) | 9758 | 432 | 4282 | 58 |
| H(22B) | 10807 | 1509 | 4237 | 58 |
| H(23) | 11378 | 1444 | 4637 | 72 |
| H(24A) | 9499 | 623 | 4793 | 116 |
| H(24B) | 10707 | −199 | 4873 | 116 |
| H(24C) | 9785 | −726 | 4673 | 116 |
| H(25A) | 12535 | 275 | 4360 | 143 |
| H(25B) | 11650 | −943 | 4407 | 143 |
| H(25C) | 12569 | −423 | 4607 | 143 |
| H(8A) | 8675 | 1676 | 4516 | 47 |
| H(22C) | 10829 | 1925 | 4201 | 53 |
| H(22D) | 11139 | 1805 | 4473 | 53 |
| H(23A) | 9487 | −35 | 4272 | 60 |
| H(24D) | 11220 | −73 | 4021 | 131 |
| H(24E) | 11102 | −1384 | 4162 | 131 |
| H(24F) | 12154 | −353 | 4235 | 131 |
| H(25D) | 9749 | −37 | 4672 | 115 |
| H(25E) | 11248 | −277 | 4643 | 115 |
| H(25F) | 10254 | −1353 | 4565 | 115 |

TABLE 11-continued

| | x | y | z | U(eq) |
|---|---|---|---|---|
| H(1A) | 2438 | 5092 | 4428 | 59 |
| H(12A) | 2759 | 3830 | 3994 | 81 |
| H(26A) | 3540 | 5106 | 3607 | 94 |
| H(26B) | 2110 | 5161 | 3709 | 94 |
| H(27A) | 2665 | 7269 | 3750 | 87 |
| H(27B) | 4142 | 6932 | 3800 | 87 |
| H(28A) | 3318 | 7292 | 4176 | 79 |
| H(28B) | 2030 | 6508 | 4118 | 79 |
| H(1AA) | 2429 | 5111 | 4416 | 59 |
| H(12B) | 3098 | 3762 | 4055 | 52 |
| H(26C) | 2281 | 4774 | 3677 | 52 |
| H(26D) | 1521 | 4708 | 3921 | 52 |
| H(27C) | 1645 | 6864 | 3888 | 52 |
| H(27D) | 2944 | 6802 | 3740 | 52 |
| H(28C) | 3961 | 7225 | 4070 | 52 |
| H(28D) | 2705 | 6946 | 4222 | 52 |
| H(1WA) | 11210(40) | 7330(40) | 5015(6) | 66(11) |
| H(1WB) | 12420(40) | 7070(40) | 4946(7) | 66(11) |
| H(2WA) | 10222 | 4575 | 4089 | 93 |
| H(2WB) | 10004 | 4017 | 3890 | 93 |
| H(3N) | 7800(30) | 5110(30) | 4628(5) | 31(7) |
| H(4N) | 8810(30) | 3070(30) | 4808(5) | 45(8) |
| H(5N) | 8880(30) | 2270(30) | 4064(5) | 47(8) |
| H(6N) | 5570(30) | 4790(40) | 4090(6) | 65(10) |

Hydrogen coordinates ($\times 10^4$) and isotropic displacement parameters ($\text{Å}^2 \times 10^3$) for d15126.

TABLE 12

| | |
|---|---|
| C(2)—N(1)—N(2)—C(3) | −0.5(3) |
| N(2)—N(1)—C(2)—O(1) | 0.1(3) |
| N(2)—N(1)—C(2)—C(1A) | 178.9(3) |
| N(2)—N(1)—C(2)—C(1) | 178.9(3) |
| C(3)—O(1)—C(2)—N(1) | 0.4(3) |
| C(3)—O(1)—C(2)—C(1A) | −178.7(2) |
| C(3)—O(1)—C(2)—C(1) | −178.7(2) |
| N(1)—N(2)—C(3)—O(1) | 0.7(3) |
| N(1)—N(2)—C(3)—C(4) | 176.2(2) |
| C(2)—O(1)—C(3)—N(2) | −0.7(3) |
| C(2)—O(1)—C(3)—C(4) | −176.8(2) |
| C(5)—N(3)—C(4)—C(3) | −138.0(2) |
| C(5)—N(3)—C(4)—C(15) | 99.5(2) |
| N(2)—C(3)—C(4)—N(3) | 117.6(3) |
| O(1)—C(3)—C(4)—N(3) | −67.1(2) |
| N(2)—C(3)—C(4)—C(15) | −119.6(3) |
| O(1)—C(3)—C(4)—C(15) | 55.7(3) |
| C(4)—N(3)—C(5)—O(2) | 1.0(3) |
| C(4)—N(3)—C(5)—C(6) | 179.11(19) |
| C(7)—N(4)—C(6)—C(5) | 77.7(3) |
| O(2)—C(5)—C(6)—N(4) | −174.5(2) |
| N(3)—C(5)—C(6)—N(4) | 7.3(3) |
| C(6)—N(4)—C(7)—O(3) | 1.4(4) |
| C(6)—N(4)—C(7)—C(8A) | −179.9(2) |
| C(6)—N(4)—C(7)—C(8) | −179.9(2) |
| C(8A)—N(5)—C(9)—O(4) | 0.4(4) |
| C(8)—N(5)—C(9)—O(4) | 0.4(4) |
| C(8A)—N(5)—C(9)—C(10) | 179.8(3) |
| C(8)—N(5)—C(9)—C(10) | 179.8(3) |
| C(11)—N(6)—C(10)—C(9) | −125.9(3) |
| O(4)—C(9)—C(10)—N(6) | −12.6(4) |
| N(5)—C(9)—C(10)—N(6) | 168.0(2) |
| C(10)—N(6)—C(11)—O(5) | −8.2(5) |
| C(10)—N(6)—C(11)—C(12A) | 173.2(8) |
| C(10)—N(6)—C(11)—C(12) | 174.3(3) |
| N(3)—C(4)—C(15)—C(16) | 174.0(2) |
| C(3)—C(4)—C(15)—C(16) | 51.3(3) |
| C(4)—C(15)—C(16)—C(17) | −113.8(3) |
| C(4)—C(15)—C(16)—C(21) | 64.2(3) |
| C(21)—C(16)—C(17)—C(18) | 1.7(4) |
| C(15)—C(16)—C(17)—C(18) | 179.8(2) |
| C(16)—C(17)—C(18)—C(19) | −0.4(4) |
| C(17)—C(18)—C(19)—C(20) | −1.3(5) |
| C(18)—C(19)—C(20)—C(21) | 1.7(5) |
| C(19)—C(20)—C(21)—C(16) | −0.3(4) |
| C(17)—C(16)—C(21)—C(20) | −1.3(4) |
| C(15)—C(16)—C(21)—C(20) | −179.5(2) |
| C(9)—N(5)—C(8)—C(7) | −58.8(3) |
| C(9)—N(5)—C(8)—C(22) | 173.2(3) |
| O(3)—C(7)—C(8)—N(5) | −53.6(3) |
| N(4)—C(7)—C(8)—N(5) | 127.7(2) |
| O(3)—C(7)—C(8)—C(22) | 69.6(4) |
| N(4)—C(7)—C(8)—C(22) | −109.1(4) |
| N(5)—C(8)—C(22)—C(23) | −178.5(4) |
| C(7)—C(8)—C(22)—C(23) | 57.1(6) |
| C(8)—C(22)—C(23)—C(24) | 63.6(6) |
| C(8)—C(22)—C(23)—C(25) | −171.9(5) |
| C(9)—N(5)—C(8A)—C(7) | −58.8(3) |
| C(9)—N(5)—C(8A)—C(22A) | −165.4(4) |
| O(3)—C(7)—C(8A)—N(5) | −53.6(3) |
| N(4)—C(7)—C(8A)—N(5) | 127.7(2) |
| O(3)—C(7)—C(8A)—C(22A) | 60.5(4) |
| N(4)—C(7)—C(8A)—C(22A) | −118.2(4) |
| N(5)—C(8A)—C(22A)—C(23A) | −91.1(6) |
| C(7)—C(8A)—C(22A)—C(23A) | 154.1(6) |
| C(8A)—C(22A)—C(23A)—C(24A) | 151.3(8) |
| C(8A)—C(22A)—C(23A)—C(25A) | −82.5(9) |
| N(1)—C(2)—C(1)—N(7) | 126.3(3) |
| O(1)—C(2)—C(1)—N(7) | −54.9(4) |
| N(1)—C(2)—C(1)—C(13) | −110.1(3) |
| O(1)—C(2)—C(1)—C(13) | 68.7(3) |
| C(14)—C(13)—C(1)—N(7) | 173.4(3) |
| C(14)—C(13)—C(1)—C(2) | 54.4(3) |
| C(2)—C(1)—N(7)—C(28) | −75.4(3) |
| C(13)—C(1)—N(7)—C(28) | 164.1(3) |
| C(2)—C(1)—N(7)—C(12) | 154.2(3) |
| C(13)—C(1)—N(7)—C(12) | 33.7(4) |
| C(28)—N(7)—C(12)—C(11) | 135.0(4) |
| C(1)—N(7)—C(12)—C(11) | −92.3(5) |
| C(28)—N(7)—C(12)—C(26) | 16.3(5) |
| C(1)—N(7)—C(12)—C(26) | 149.0(4) |
| O(5)—C(11)—C(12)—N(7) | 170.7(3) |
| N(6)—C(11)—C(12)—N(7) | −11.7(5) |
| O(5)—C(11)—C(12)—C(26) | −72.8(5) |
| N(6)—C(11)—C(12)—C(26) | 104.8(4) |
| N(7)—C(12)—C(26)—C(27) | 11.6(5) |
| C(11)—C(12)—C(26)—C(27) | −110.1(4) |
| C(12)—C(26)—C(27)—C(28) | −33.3(5) |
| C(1)—N(7)—C(28)—C(27) | −173.7(4) |
| C(12)—N(7)—C(28)—C(27) | −37.4(5) |
| C(26)—C(27)—C(28)—N(7) | 43.4(4) |
| N(1)—C(2)—C(1A)—N(7A) | 131.2(8) |
| O(1)—C(2)—C(1A)—N(7A) | −50.0(8) |
| N(1)—C(2)—C(1A)—C(13) | −110.1(3) |
| O(1)—C(2)—C(1A)—C(13) | 68.7(3) |
| C(14)—C(13)—C(1A)—N(7A) | 166.8(7) |
| C(14)—C(13)—C(1A)—C(2) | 54.4(3) |
| C(2)—C(1A)—N(7A)—C(28A) | −72.4(12) |
| C(13)—C(1A)—N(7A)—C(28A) | 170.9(12) |
| C(2)—C(1A)—N(7A)—C(12A) | 159.8(10) |
| C(13)—C(1A)—N(7A)—C(12A) | 43.0(13) |
| O(5)—C(11)—C(12A)—N(7A) | 171.3(6) |
| N(6)—C(11)—C(12A)—N(7A) | −10.1(14) |
| O(5)—C(11)—C(12A)—C(26A) | −43(3) |
| N(6)—C(11)—C(12A)—C(26A) | 135(2) |
| C(28A)—N(7A)—C(12A)—C(11) | 129.1(18) |
| C(1A)—N(7A)—C(12A)—C(11) | −101.7(19) |
| C(28A)—N(7A)—C(12A)—C(26A) | −27.4(17) |
| C(1A)—N(7A)—C(12A)—C(26A) | 101.7(15) |
| C(11)—C(12A)—C(26A)—C(27A) | −114(3) |
| N(7A)—C(12A)—C(26A)—C(27A) | 33.9(18) |
| C(12A)—C(26A)—C(27A)—C(28A) | −29(2) |
| C(1A)—N(7A)—C(28A)—C(27A) | −122.4(18) |
| C(12A)—N(7A)—C(28A)—C(27A) | 10(2) |
| C(26A)—C(27A)—C(28A)—N(7A) | 13(2) |

Symmetry transformations used to generate equivalent atoms:

Torsion angles [°] for d15126.

TABLE 13

| D-H...A | d(D-H) | d(H...A) | d(D...A) | <(DHA) |
|---|---|---|---|---|
| O(1W)—H(1WA)...O(2) | 0.85(4) | 1.99(4) | 2.837(3) | 175(4) |
| O(1W)—H(1WB)...N(1)#1 | 0.85(4) | 2.09(4) | 2.909(3) | 164(4) |
| O(2W)—H(2WA)...O(3) | 0.84 | 1.96 | 2.805(4) | 179.6 |
| O(2W)—H(2WB)...O(5)#2 | 0.84 | 2.18 | 3.022(5) | 179.7 |
| N(3)—H(3N)...O(4) | 0.89(3) | 2.13(3) | 2.988(3) | 162(2) |
| N(4)—H(4N)...O(1W)#3 | 0.87(3) | 2.00(3) | 2.867(3) | 178(3) |
| N(5)—H(5N)...O(5)#2 | 0.88(3) | 1.99(3) | 2.854(3) | 166(3) |
| N(6)—H(6N)...O(1) | 0.88(4) | 2.59(4) | 3.416(3) | 158(3) |
| N(6)—H(6N)...N(7) | 0.88(4) | 2.17(4) | 2.713(4) | 119(3) |
| N(6)—H(6N)...N(7A) | 0.88(4) | 2.03(4) | 2.592(18) | 121(3) |

Symmetry transformations used to generate equivalent atoms:

1 x+1,y,z  #2 x+½, −y+½, −z+¾  #3 y,x−1, −z+1

Hydrogen bonds for d15126 [Å and °].

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

1. Wessjohann, L. A.; Ruijter, E.; Garcia-Rivera, D.; Brandt, W., What can a chemist learn from nature's macrocycles?—a brief, conceptual view. *Molecular Diversity* 2005, 9 (1-3), 171-86.
2. Driggers, E. M.; Hale, S. P.; Lee, J.; Terrett, N. K., The exploration of macrocycles for drug discovery—an underexploited structural class. *Nat Rev Drug Discov* 2008, 7 (7), 608-24.
3. Marsault, E.; Peterson, M. L., Macrocycles are great cycles: applications, opportunities, and challenges of synthetic macrocycles in drug discovery. *Journal of Medicinal Chemistry* 2011, 54 (7), 1961-2004.
4. Katsara, M.; Tselios, T.; Deraos, S.; Deraos, G.; Matsoukas, M. T.; Lazoura, E.; Matsoukas, J.; Apostolopoulos, V., Round and round we go: cyclic peptides in disease. *Curr Med Chem* 2006, 13 (19), 2221-32.
5. Nolan, E. M.; Walsh, C. T., How nature morphs peptide scaffolds into antibiotics. *Chembiochem* 2009, 10 (1), 34-53.
6. Schreiber, S. L.; Crabtree, G. R., The mechanism of action of cyclosporin A and FK506. *Immunol Today* 1992, 13 (4), 136-42.
7. Hili, R.; Yudin, A. K., Readily available unprotected amino aldehydes. *Journal of the American Chemical Society* 2006, 128 (46), 14772-3.
8. Hili, R.; Rai, V.; Yudin, A. K., Macrocyclization of linear peptides enabled by amphoteric molecules. *Journal of the American Chemical Society* 2010, 132 (9), 2889-91.
9. Zaretsky, S.; Scully, C. C. G.; Lough, A. J.; Yudin, A. K., Exocyclic Control of Turn Induction in Macrocyclic Peptide Scaffolds. *Chemistry—a European Journal* 2013, 19 (52), 17668-17672.
10. Assem, N.; Hili, R.; He, Z.; Kasahara, T.; Inman, B. L.; Decker, S.; Yudin, A. K., Role of reversible dimerization in reactions of amphoteric aziridine aldehydes. *Journal of Organic Chemistry* 2012, 77 (13), 5613-23.
11. Weinberger, B.; Fehlhammer, W. P., Metal-Complexes of Functional Isocyanides 0.4. "N-Isocyanoiminotriphenylphosphorane—Synthesis, Coordination Chemistry, and Reactions at the Metal. *Angewandte Chemie-International Edition in English* 1980, 19 (6), 480-481.
12. Stolzenberg, H.; Weinberger, B.; Fehlhammer, W. P.; Puhlhofer, F. G.; Weiss, R., Free and metal-coordinated (N-isocyanimino)triphenylphosphorane: X-ray structures and selected reactions. *European Journal of Inorganic Chemistry* 2005, (21), 4263-4271.
13. Ramazani, A.; Rezaei, A., Novel one-pot, four-component condensation reaction: an efficient approach for the synthesis of 2,5-disubstituted 1,3,4-oxadiazole derivatives by a Ugi-4CR/aza-Wittig sequence. *Organic Letters* 2010, 12 (12), 2852-5.
14. Borg, S.; Estennebouhtou, G.; Luthman, K.; Csoregh, I.; Hesselink, W.; Hacksell, U., Synthesis of 1,2,4-Oxadiazole-Derived, 1,3,4-Oxadiazole-Derived, and 1,2,4-Triazole-Derived Dipeptidomimetics. *Journal of Organic Chemistry* 1995, 60 (10), 3112-3120.
15. Frank, A. T.; Farina, N. S.; Sawwan, N.; Wauchope, O. R.; Qi, M.; Brzostowska, E. M.; Chan, W.; Grasso, F. W.; Haberfield, P.; Greer, A., Natural macrocyclic molecules have a possible limited structural diversity. *Molecular Diversity* 2007, 11 (3-4), 115-118.
16. Ovadia, O.; Greenberg, S.; Chatterjee, J.; Laufer, B.; Opperer, F.; Kessler, H.; Gilon, C.; Hoffman, A., The effect of multiple N-methylation on intestinal permeability of cyclic hexapeptides. *Mol Pharm* 2011, 8 (2), 479-87.
17. Hewitt, W. M.; Leung, S. S.; Pye, C. R.; Ponkey, A. R.; Bednarek, M.; Jacobson, M. P.; Lokey, R. S., Cell-permeable cyclic peptides from synthetic libraries inspired by natural products. *Journal of the American Chemical Society* 2015, 137 (2), 715-21.
18. Cody, W. L.; He, J. X.; Reily, M. D.; Haleen, S. J.; Walker, D. M.; Reyner, E. L.; Stewart, B. H.; Doherty, A. M., Design of a potent combined pseudopeptide endothelin-A/endothelin-B receptor antagonist, Ac-DBhg16-Leu-Asp-Ile-[NMe]Ile-Trp21 (PD 156252): examination of its pharmacokinetic and spectral properties. *Journal of Medicinal Chemistry* 1997, 40 (14), 2228-40.
19. Haviv, F.; Fitzpatrick, T. D.; Nichols, C. J.; Swenson, R. E.; Mort, N. A.; Bush, E. N.; Diaz, G.; Nguyen, A. T.; Holst, M. R.; Cybulski, V. A.; Leal, J. A.; Bammert, G.; Rhutasel, N. S.; Dodge, P. W.; Johnson, E. S.; Cannon, J. B.; Knittle, J.; Greer, J., The Effect of Nmetyr(5) Substitution in Luteinizing-Hormone-Releasing Hormone Antagonists. *Journal of Medicinal Chemistry* 1993, 36 (7), 928-933.
20. Haviv, F.; Fitzpatrick, T. D.; Swenson, R. E.; Nichols, C. J.; Mort, N. A.; Bush, E. N.; Diaz, G.; Bammert, G.; Nguyen, A.; Rhutasel, N. S.; Nellans, H. N.; Hoffman, D. J.; Johnson, E. S.; Greer, J., Effect of N-Methyl Substitution of the Peptide-Bonds in Luteinizing-Hormone-Releasing Hormone Agonists. *Journal of Medicinal Chemistry* 1993, 36 (3), 363-369.
21. Ali, F. E.; Bennett, D. B.; Calvo, R. R.; Elliott, J. D.; Hwang, S. M.; Ku, T. W.; Lago, M. A.; Nichols, A. J.; Romoff, T. T.; Shah, D. H.; Vasko, J. A.; Wong, A. S.; Yellin, T. O.; Yuan, C. K.; Samanen, J. M., Conformationally Constrained Peptides and Semipeptides Derived from Rgd as Potent Inhibitors of the Platelet Fibrinogen Receptor and Platelet-Aggregation. *Journal of Medicinal Chemistry* 1994, 37 (6), 769-780.

22. Biron, E.; Chatterjee, J.; Ovadia, O.; Langenegger, D.; Brueggen, J.; Hoyer, D.; Schmid, H. A.; Jelinek, R.; Gilon, C.; Hoffman, A.; Kessler, H., Improving oral bioavailability of peptides by multiple N-methylation: Somatostatin analogues. *Angewandte Chemie-International Edition* 2008, 47 (14), 2595-2599.

23. Doedens, L.; Opperer, F.; Cai, M.; Beck, J. G.; Dedek, M.; Palmer, E.; Hruby, V. J.; Kessler, H., Multiple N-methylation of MT-II backbone amide bonds leads to melanocortin receptor subtype hMC1R selectivity: pharmacological and conformational studies. *Journal of the American Chemical Society* 2010, 132 (23), 8115-28.

24. Mas-Moruno, C.; Rechenmacher, F.; Kessler, H., Cilengitide: the first anti-angiogenic small molecule drug candidate design, synthesis and clinical evaluation. *Anticancer Agents Med Chem* 2010, 10 (10), 753-68.

25. White, T. R.; Renzelman, C. M.; Rand, A. C.; Rezai, T.; McEwen, C. M.; Gelev, V. M.; Turner, R. A.; Linington, R. G.; Leung, S. S. F.; Kalgutkar, A. S.; Bauman, J. N.; Zhang, Y. Z.; Liras, S.; Price, D. A.; Mathiowetz, A. M.; Jacobson, M. P.; Lokey, R. S., On-resin N-methylation of cyclic peptides for discovery of orally bioavailable scaffolds. *Nat Chem Biol* 2011, 7(11), 810-817.

26. He, Z.; Yudin, A. K., Amphoteric alpha-Boryl Aldehydes. *Journal of the American Chemical Society* 2011, 133 (35), 13770-13773.

27. Bio, M. M.; Javadi, G.; Song, Z. J., An improved synthesis of N-isocyanoiminotriphenylphosphorane and its use in the preparation of diazoketones. *Synthesis-Stuttgart* 2005, (1), 19-21.

---

The invention claimed is:

1. A cyclic amino acid molecule of formula [(I)] or a salt of the foregoing:

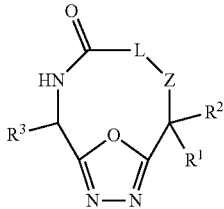

[(I)]

wherein,
- Z is an amino terminus of an amino acid;
- —C=O— is a carboxy terminus of an amino acid;
- L, along with Z and —C=O— is a linear peptide;
- $R^1$ and $R^2$ are each independently hydrogen or an organic group, and are optionally covalently linked to each other; and
- $R^3$ is an amino acid side-chain.

2. The cyclic amino acid molecule of claim 1, wherein $R^1$ and $R^2$ are each independently selected from the group consisting of hydrogen, an alkyl group, a heteroalkyl group, a cycloalkyl group, an alkenyl group, a heteroalkenyl group, an alkynyl group, a heteroalkynyl group, an aryl group, a heteroaryl group, a heterocyclic group, an acyl group, an α-MIDA borylaldehyde, $CF_3$, $CH_2$—$CF_3$, a macrocycle, a fluorophore, an orthogonal reactive group, an affinity tag, an isotopically labeled molecule, a nucleoside, a nucleotide, a lipid, a carbohydrate, a small molecule, a functionalized solid support, and a biologic.

3. The cyclic amino acid molecule of claim 1, wherein $R^1$ and $R^2$ are each independently selected from the group consisting of ethyl, benzyl and phenyl.

4. The cyclic amino acid molecule of claim 2, wherein the α-MIDA borylaldehyde is $C_6H_9BNO_4$.

5. The cyclic amino acid molecule of claim 2, wherein the orthogonal reactive group is selected from the group consisting of a cyclic alkyne, a linear alkyne, a cyclic azide, a linear azide, a cyclic tetrazole and a linear tetrazole.

6. The cyclic amino acid molecule of claim 2, wherein the affinity tag is biotin.

7. The cyclic amino acid molecule of claim 2, wherein the biologic is selected from the group consisting of a functionalized peptide, a functionalized protein, or a functionalized amino acid.

8. The cyclic amino acid molecule of claim 2, wherein the functionalized solid support is a solid surface or resin bead.

9. The cyclic amino acid molecule of claim 2, wherein the small molecule is a drug.

10. The cyclic amino acid molecule of claim 2, wherein the cyclic amino acid is a lariat type macrocycle.

11. The cyclic amino acid molecule of claim 2, wherein $R^1$ and $R^2$ are covalently linked to each other.

12. The cyclic amino acid molecule of claim 11, wherein $R^1$ and $R^2$ form a cycloalkanone.

13. The cyclic amino acid molecule of claim 1, wherein the linear peptide comprises a D or L amino acid.

14. The cyclic amino acid molecule of claim 1, wherein the linear peptide comprises an alpha-amino acid.

15. The cyclic amino acid molecule of claim 1, wherein the linear peptide comprises a beta-amino acid.

16. The cyclic amino acid molecule of claim 1, wherein the linear peptide comprises a gamma-amino acid.

17. The cyclic amino acid molecule of claim 1, wherein the cyclic amino acid comprises a diastereomer and a carbon atom derived from an aldehyde group is a stereocenter.

18. The cyclic amino acid molecule of claim 17, wherein the stereocenter has an (S) configuration diastereomer.

19. The cyclic amino acid molecule of claim 17, wherein the stereocenter has an (R) configuration diastereomer.

20. The cyclic amino acid molecule of claim 1, wherein the linear peptide comprises at least 2 amino acids, 3 amino acids, 4 amino acids, 5 amino acids, 6 amino acids, 7 amino acids, or 8 amino acids.

21. A process to produce the cyclic amino acid molecule of claim 1 comprising reacting a linear peptide or a salt thereof, having an amino terminus and a carboxyl terminus, with an isocyano-iminophosphorane having the formula (II):

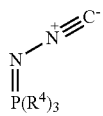
(II)

and a compound having the formula (III):

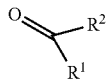
(III)

wherein,

R$^1$ and R$^2$ are each independently hydrogen or an organic group, and are optionally covalently linked to each other; and each R$^4$ is independently an organic group.

22. The process of claim 21, wherein at least one R$^4$ is Ph.

23. The process of claim 22, wherein all R$^4$ are Ph.

24. The process of claim 22, wherein each R$^4$ is independently selected from the group consisting of an alkyl, an aryl and an alkoxy.

25. The process of claim 21, further comprising conjugating a fluorescent tag to the cyclic molecule.

26. The process of claim 21, further comprising deprotecting one or more side chains of the cyclic amino acid molecule if one or more of said side chains are protected with protecting groups.

27. The cyclic amino acid molecule of claim 11, wherein R$^1$ and R$^2$ form a cyclopentanone.

* * * * *

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Gly Leu Gly Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Gly Leu Gly Phe
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Gly Leu Gly Phe
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Ser Leu Tyr Gly
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Asp Ala Trp Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Leu Asp Phe Ala
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Phe Asp Leu Ala
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Ala Leu Ala Phe
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Phe Leu Asp Ala
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Pro Gly Leu Ala Phe
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Ala Leu Gly Phe
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Leu Phe Asp Ala
1               5
```